(12) United States Patent
Sotereanos

(10) Patent No.: US 7,247,171 B2
(45) Date of Patent: *Jul. 24, 2007

(54) MODULAR HIP IMPLANTS

(76) Inventor: Nicholas G. Sotereanos, 2335 Buena Vista Dr., McKeesport, PA (US) 15135

( * ) Notice: Subject to any disclaimer, the term of this patent is extended or adjusted under 35 U.S.C. 154(b) by 773 days.

This patent is subject to a terminal disclaimer.

(21) Appl. No.: 10/095,181

(22) Filed: Mar. 11, 2002

(65) Prior Publication Data

US 2003/0171819 A1    Sep. 11, 2003

(51) Int. Cl.
*A61F 2/32* (2006.01)

(52) U.S. Cl. .................................. 623/22.42

(58) Field of Classification Search ............ 623/11.11, 623/16.11, 18.11, 22.11, 22.4, 22.42, 22.43, 623/22.44, 22.46, 23.11, 23.15, 23.26, 23.27, 623/23.32, 23.33, 23.6, 23.57; 606/60, 62, 606/63, 64, 65, 66, 67, 68
See application file for complete search history.

(56) References Cited

U.S. PATENT DOCUMENTS

| | | | |
|---|---|---|---|
| 2,682,265 A | 6/1954 | Collison | |
| 2,718,228 A | 9/1955 | Van Steenbrugghe | |
| 2,785,673 A | 3/1957 | Anderson | |
| 3,433,220 A * | 3/1969 | Zickel | 606/67 |
| 4,005,495 A | 2/1977 | Lock et al. | |
| 4,080,666 A | 3/1978 | Fixel | |
| 4,101,985 A * | 7/1978 | Baumann et al. | 623/22.46 |
| 4,129,903 A | 12/1978 | Huggler | |
| 4,530,114 A | 7/1985 | Tepic | |
| 4,532,660 A | 8/1985 | Field | |
| 4,714,478 A | 12/1987 | Fischer | |
| 4,752,296 A | 6/1988 | Buechel et al. | |
| 4,795,473 A | 1/1989 | Grimes | |
| 4,834,756 A | 5/1989 | Kenna | |
| 4,946,461 A | 8/1990 | Fischer | |
| 4,957,510 A | 9/1990 | Cremascoli | |
| 4,963,155 A * | 10/1990 | Lazzeri et al. | 623/22.42 |
| 4,976,740 A | 12/1990 | Kleiner | |
| 4,994,085 A | 2/1991 | Sawai et al. | |
| 4,995,883 A * | 2/1991 | Demane et al. | 623/22.42 |

(Continued)

FOREIGN PATENT DOCUMENTS

DE        200 07 950 U1    8/2000

(Continued)

*Primary Examiner*—Anu Ramana
(74) *Attorney, Agent, or Firm*—Kirkpatrick & Lockhart Preston Gates Ellis LLP

(57) ABSTRACT

An implant for improved engagement between modular components is provided. The implant includes a body member for insertion, in use, in a natural femoral neck; and a rod for insertion, in use, in the intramedullary canal of a femur. The body member has a first engagement surface and the rod has a second engagement surface such that the first and second engagement surfaces are configured for complementary engagement with each other. One of the first or second engagement surfaces may be a protrusion while the other of the first or second engagement surfaces may be a recess for receiving the protrusion. The implant may further include a locking member, a stabilizing member and a guide means. A domed head portion is provided for attachment to a medial end of the body member and insertion, in use, in a natural or prosthetic acetabulum.

71 Claims, 19 Drawing Sheets

U.S. PATENT DOCUMENTS

| | | | |
|---|---|---|---|
| 4,998,937 A * | 3/1991 | Grimes | 606/89 |
| 5,007,935 A | 4/1991 | Vincent et al. | |
| 5,080,685 A * | 1/1992 | Bolesky et al. | 623/22.42 |
| 5,087,260 A | 2/1992 | Fixel | |
| 5,100,407 A | 3/1992 | Conrad et al. | |
| 5,116,379 A * | 5/1992 | McLardy-Smith | 623/22.42 |
| 5,133,772 A | 7/1992 | Hack et al. | |
| 5,314,479 A * | 5/1994 | Rockwood et al. | 623/19.14 |
| 5,336,268 A | 8/1994 | Rispeter | |
| 5,342,366 A | 8/1994 | Whiteside et al. | |
| 5,389,107 A | 2/1995 | Nassar et al. | |
| 5,458,654 A | 10/1995 | Tepic | |
| 5,571,203 A | 11/1996 | Masini | |
| 5,593,451 A | 1/1997 | Averill et al. | |
| 5,725,595 A | 3/1998 | Gustilo | |
| 5,755,810 A | 5/1998 | Cunningham | |
| 5,800,553 A | 9/1998 | Albrektsson et al. | |
| 5,800,557 A | 9/1998 | Elhami | |
| 5,817,098 A | 10/1998 | Albrektsson et al. | |
| 5,876,446 A * | 3/1999 | Agrawal et al. | 623/23.61 |
| 5,888,206 A * | 3/1999 | Lob et al. | 623/18.11 |
| 5,888,208 A | 3/1999 | Ro | |
| 5,902,340 A * | 5/1999 | White et al. | 128/898 |
| 5,980,575 A | 11/1999 | Albrektsson et al. | |
| 5,997,582 A | 12/1999 | Weiss | |
| 6,010,535 A | 1/2000 | Shah | |
| 6,221,074 B1 * | 4/2001 | Cole et al. | 606/62 |
| 6,284,002 B1 * | 9/2001 | Sotereanos | 623/27 |
| 6,383,227 B1 | 5/2002 | Baround et al. | |
| 6,440,171 B1 * | 8/2002 | Doubler et al. | 623/22.42 |
| 6,616,697 B2 * | 9/2003 | Sotereanos | 623/23.26 |
| 6,682,568 B2 * | 1/2004 | Despres et al. | 623/22.42 |
| 6,695,883 B2 | 2/2004 | Crofford | |
| 6,702,854 B1 * | 3/2004 | Cheal et al. | 623/22.42 |
| 6,843,806 B2 * | 1/2005 | Hayes et al. | 623/23.22 |
| 2003/0125808 A1 * | 7/2003 | Hunter et al. | 623/18.11 |

FOREIGN PATENT DOCUMENTS

| | | |
|---|---|---|
| DE | 101 20 331 A1 | 11/2002 |
| EP | 0 010 527 A1 | 4/1980 |
| EP | 0382395 * | 8/1990 |
| EP | 1 240 879 A2 | 9/2002 |
| WO | WO 93/08770 | 5/1993 |
| WO | WO 94/17757 | 8/1994 |
| WO | WO 00/72785 A2 | 12/2000 |
| WO | WO 01/49218 | 7/2001 |

* cited by examiner

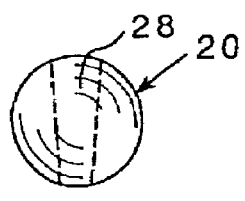 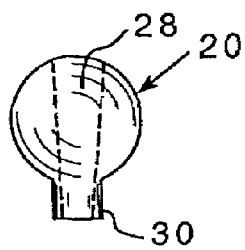 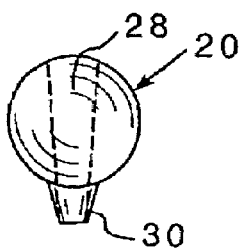 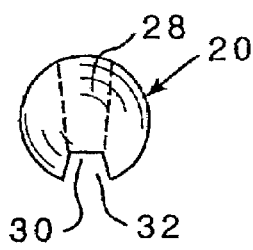
FIG. 10B        FIG. 11B        FIG. 12B        FIG. 13B
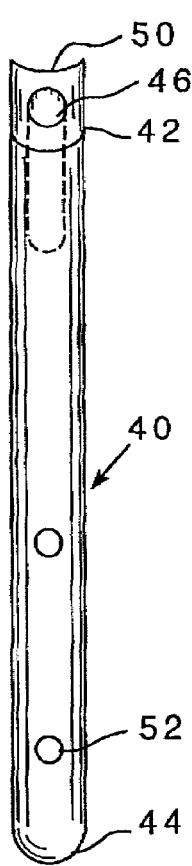 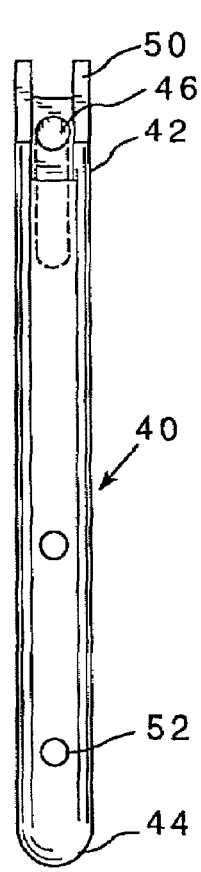 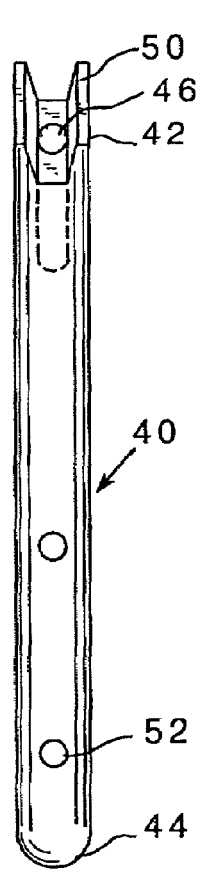 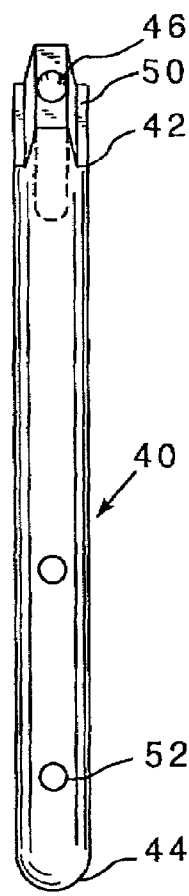
FIG. 10A        FIG. 11A        FIG. 12A        FIG. 13A

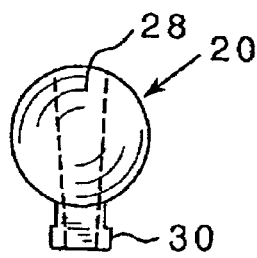 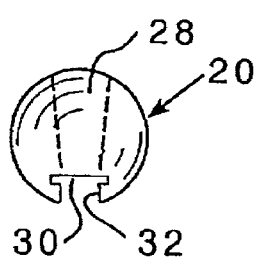 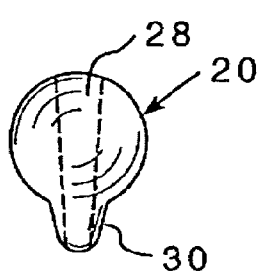 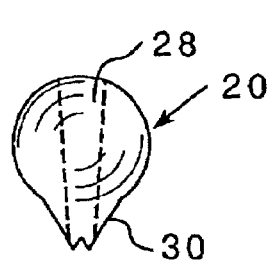
FIG. 14B    FIG. 15B    FIG. 16B    FIG. 17B
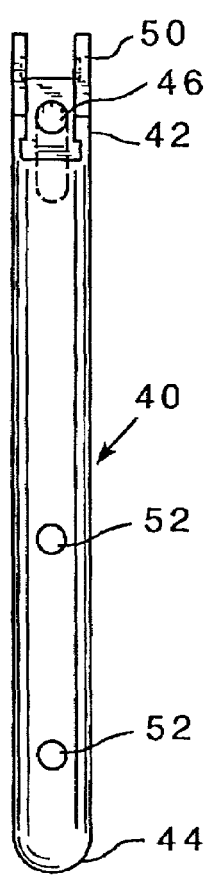 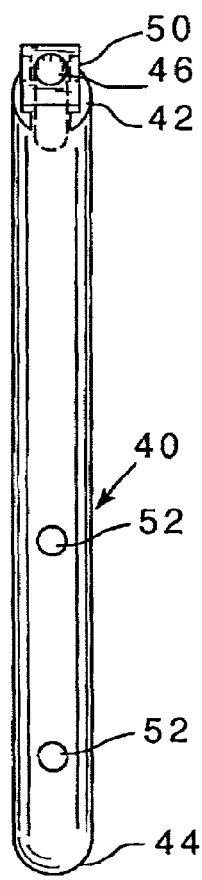 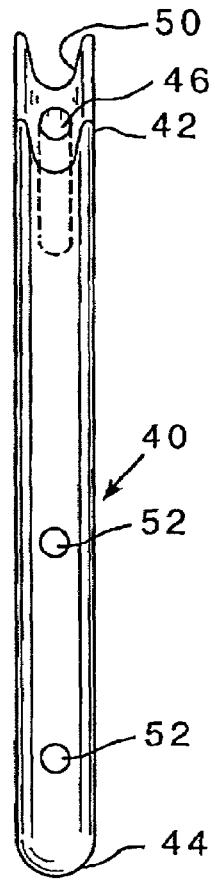 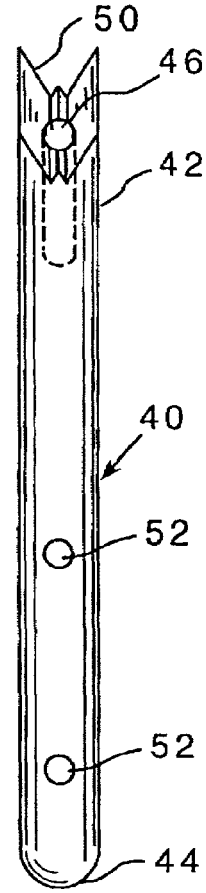
FIG. 14A    FIG. 15A    FIG. 16A    FIG. 17A

MODULAR HIP IMPLANTS

BACKGROUND OF THE INVENTION

1. Field of the Invention

The subject invention relates to prosthetic implants, and, more particularly, to a modular implant for total hip replacement.

2. Description of the Invention Background

Hip replacements have become common. A person's hip joint may need to be replaced due to degeneration from disease or from severe trauma. If the degeneration or injury is severe, replacement of the natural joint, in whole or in part, with a prosthesis may be necessary. While initial hip implants are generally successful, they often have to be replaced in time, sometimes because of further degeneration and sometimes because of stress to remaining bone caused by the prosthesis.

Numerous designs for total hip and shoulder replacements have been developed, but problems persist.

SUMMARY OF THE INVENTION

The implant of the present invention includes modular components comprising generally a body member, a rod and a head member. A joining portion joins the body member and the head member to each other. The body member has a medial end, a lateral end and a longitudinal axis extending between the medial and lateral ends. It is configured for positioning, in use, in a natural femoral neck, and has a first engagement surface on a side surface thereof and a joining portion on the medial end. The head member attaches to the joining portion of the body member and is configured for positioning, in use, in a natural or prosthetic acetabulum. The rod has a proximal end, a distal end and a longitudinal axis extending between the distal and proximal ends thereof and is configured for positioning, in use, in the intramedullary canal of a femur. The rod has a second engagement surface positioned in one embodiment at the proximal end of the rod and in another embodiment in a transverse passage through the rod. The second engagement surface of the rod is configured for complementary engagement with the first engagement surface of the body member. One of the first and second engagement surfaces may comprise a protrusion and the other of the first and second engagement surfaces may comprise a recess configured to receive the protrusion for constraining the body member against rotation about the longitudinal axis of the body member. In an embodiment of the invention wherein the recess is in the body member, the recess may define a channel extending from the medial end of the body member to an area intermediate the medial and lateral ends of the body member to permit the body member to slide over the protrusion of the second engagement surface as it is advanced into the bone of the femoral neck. The engagement surfaces defined by the recess and the protrusion may have a variety of shapes, including without limitation, trapezoidal, square, rectangular, dovetailed, T-shaped, pyramidal, curved and irregularly shaped in cross section.

The body member and the rod may also form, in cross section, a variety of shapes to constrain the body member and rod against rotation about their respective longitudinal axes. Either or both of the body member and the rod may therefore be fluted, scalloped, square or diamond shaped, or triangular in cross section, or other suitable shapes.

Alternatively, the body member may be cylindrical and the proximal end of the rod may form a concave channel configured to seat the cylindrical surface of the body member. In this embodiment, the body member may rotate about its axis unless secured against rotation by means of a setscrew, fastener or other locking member. The body member may include a passage in a direction transverse to the longitudinal axis of the body member to receive the locking member. The rod may also include a locking passage for locking the body member to the rod. The locking passage, if formed, passes through at least a portion of the rod, and preferably through the second engagement surface of the rod, and is positioned such that the passage in the body member and the locking passage in the rod are coaxially aligned relative to each other. A fastener, set screw or other locking member may be provided for passage through the passage in the body member and into the locking passage of the rod to further secure the body member to the rod.

In another embodiment of the invention, the rod may be elongate in shape and define a transverse passage structured for sliding engagement with the body member passes. The transverse passage in this embodiment is angled to position the body member, in use, through the femoral neck and towards the femoral head. As mentioned above, the interior of the transverse passage includes a second engagement surface for engaging the first engagement surface of the body member. As described above, one of the first and second engagement surfaces may form a recess and the other a protrusion to define complementary engagement surfaces. In this embodiment, a setscrew, tapered wedge or other locking member may be used to secure the body member in the desired position within the transverse passage of the rod.

The implant may also include a passage through at least a portion of the rod in a direction transverse to the longitudinal axis of the rod for stabilizing the implant in a femur. The implant may further comprise a stabilizing member for passage through the passage in the rod. The stabilizing member may be a bone screw or other fastener.

The rod may also include a guide passage to assist in guiding the rod into the proper position within the femur. The guide passage is generally coaxial to the longitudinal axis of the rod and is wide enough to permit the rod to be inserted onto a guide wire, and, thereafter, for the guide wire to be removed by pulling the guide wire from the guide passage of the rod.

In addition to the various embodiments of the present invention described above, the implant may also include features and embodiments including, but not limited to, a collar at the lateral end of the body member, a porous coating on the body member to promote bone in-growth, a porous coating on the rod to promote bone in-growth, a second layer of a coating on one or both of the rod and body member, and a sleeve for positioning over the joining portion of the body member for adjusting the angle or position of the head member relative to the longitudinal axis of the body member, as described in U.S. Pat. Nos. 6,284, 002 and 6,616,697, both of which are incorporated herein by reference.

The present invention also includes a method for inserting the implant. The method comprises forming a first incision on the lateral side of the patient's hip over the flare of the greater trochanter, forming a second incision over the patient's proximal hip, near the waist, resecting the head of the femur, reaming the intramedullary canal of the femur through the second incision, inserting a guide wire into the intramedullary canal of the femur, and sliding the rod described above over the guide-wire into the intramedullary canal of the femur. The reamed canal may be narrower than the outer dimension of the rod to allow the rod to be pressure fit into the intramedullary canal. When the rod is in a desired position, the guide wire is removed.

The method further includes forming a passage from the base of the greater trochanter along the longitudinal axis of the natural femoral neck, providing a body member having a medial end, a lateral end and a longitudinal axis extending between the medial and lateral ends, and an engagement surface on a distal side surface thereof and a joining portion on the medial end thereof, inserting the medial end of the body member through the second incision, and advancing the body member through the passage, aligning the engagement surfaces of the rod and the body member and continuing to advance the body member through the passage to a desired position. The method may further include locking the body member in the desired position, and securing a prosthetic femoral head to the joining portion of the body member. Locking the body member in the desired position may be done, for example, by inserting a locking member or any suitable fastening means into a locking passage through the body member and into the rod.

Other details, objects and advantages of the present invention will become apparent with the following description of the present invention.

BRIEF DESCRIPTION OF THE SEVERAL VIEWS OF THE DRAWINGS

For the purpose of illustrating the preferred embodiments of the implant of the present invention and not for limiting the same, reference is made to the drawings in which:

FIGS. 10A, B through 17A, B illustrate different embodiments of complementary engagement surfaces on a rod and body member. FIGS. 10A through 17A illustrate rods. FIGS. 10B through 17B illustrate cross-sectional views of body members structured for use with the rod of the same Figure.

FIG. 18A shows a body member with a narrowed lateral side and one transverse passage. FIG. 18B shows a body member with a collar, two transverse passages and beading on the exterior surface of the rod. FIG. 18C shows a sleeve for extending the length or altering the angle of the joining portion of the body member. FIG. 18D shows a head member. FIG. 18E shows another embodiment of a larger head member having a wider recess for receiving the sleeve.

DETAILED DESCRIPTION OF THE INVENTION

Figure 1A:
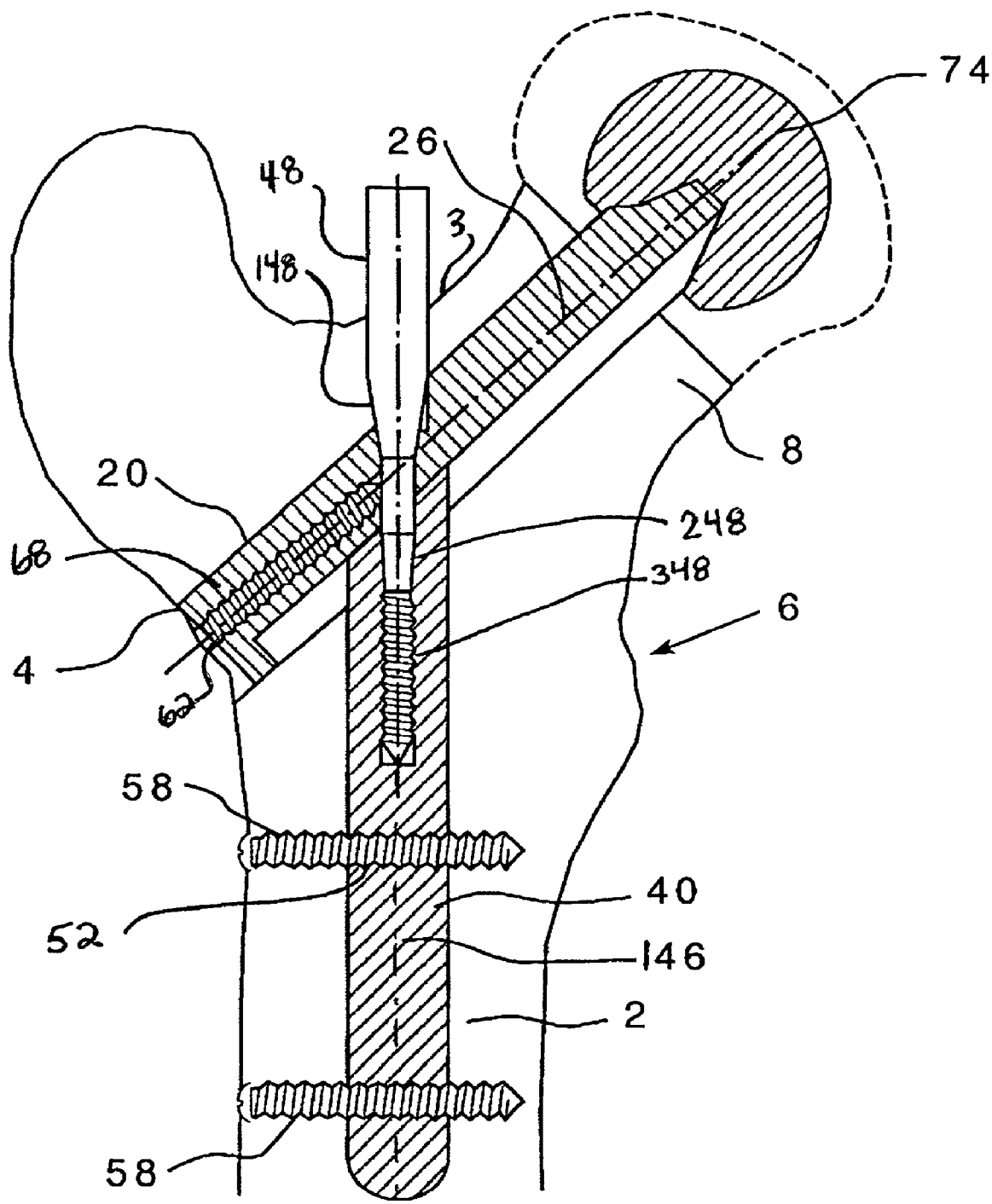
FIG. 1A is a cross-sectional view of an assembled embodiment of the implant of the present invention shown as implanted in a femur.

FIGS. 1 through 30 illustrate various embodiments of the implant 10 of the present invention. Referring to FIGS. 1A and B, an assembled embodiment of the implant 10 is shown, as it would appear after implantation in a femur 6. The natural femoral head, illustrated by dashed lines, has been removed, but the femoral neck 8 and the remainder of the femur 6 remain intact.

The implant 10 of the present invention includes modular components, generally a body member 20, a rod 40 and a domed head member 74.

Generally, the body member 20 is configured for positioning, in use, in a natural femoral neck 8 such that the longitudinal axis 26 of the body member 20 is generally in co-axial alignment with the central longitudinal axis of the femoral neck 8. Some deviation from alignment with the neck axis can be tolerated and would in practice be determined by a surgeon in each case. The rod 40 is configured for positioning, in use, in the intramedullary canal 2 such that the longitudinal axis 46 of the rod 40 is generally co-axial to the central longitudinal axis of the intramedullary canal 2 of the femur 6. Some deviation from alignment with the axis of the intramedullary canal 2 can be tolerated and would in practice be determined by the surgeon in each case.

The longitudinal axis 26 of the body member 20 and the longitudinal axis 146 of the rod 40 form an angle where the axes intersect as close as possible to the patient's anatomy, usually between about 125° and 145°, and most typically about 130°.

Figure 5:
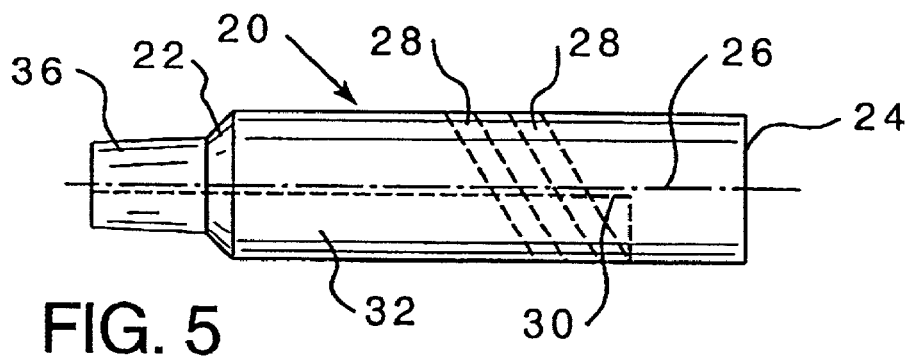
FIG. 5 is a side view of an embodiment of a body member showing two transverse passages.
Figure 8:
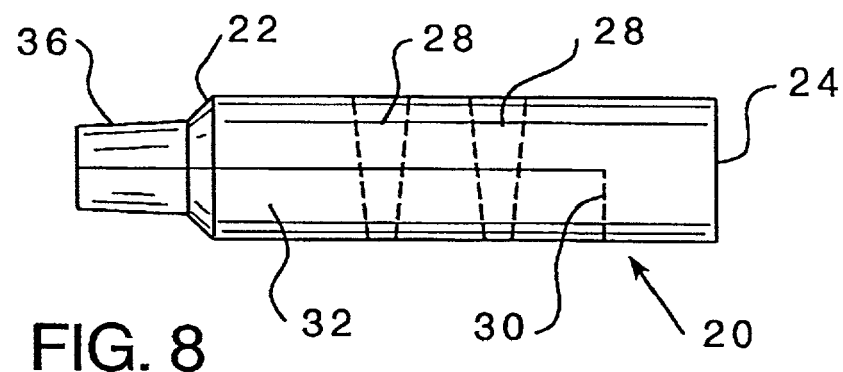
FIG. 8 is a side view of a body member for use with the rod of FIG. 7.

Referring to FIGS. 3, 5 and 8, the body member 20 has a longitudinal axis 26, a lateral end 24 and a medial end 22. In addition, the body member 20 has a first engagement surface 30. The first engagement surface 30 is configured to engage a complementary mating surface on the proximal end 42 of the rod 40. In one embodiment of the body member 20, the engagement surface 30 may form a recess on a side of the body member (the distal side, in use). As shown in the drawings, the recess may form a channel 32 extending from the medial end 22 to a location intermediate the medial and lateral ends 22, 24 of the body member 20 to allow the body member to slide into position over a complementary protrusion in the rod 40, to be described below. An alternative embodiment of the engagement surface 30 forms a protrusion that extends from one side of the body member 20. Examples of embodiments of the engagement surface 30 are shown in FIGS. 10B-17B.

Figures 3A, 3B:
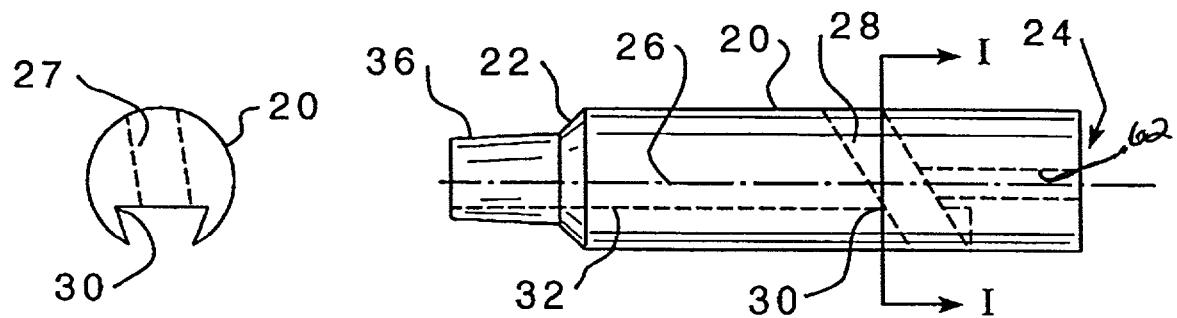
FIG. 3A is a side view of an embodiment of a body member having one transverse passage therethrough and a recess configured for engagement with the trapezoidal section of the rod of FIGS. 2A, 2B.
FIG. 3B is a section view of the embodiment of the body member of FIG. 3A though the line I-I.

The body member 20 may include passages for receipt of various locking members. As shown in FIG. 3A, body member 20 may have a passage 28 transverse to its longitudinal axis 26, for receiving a locking member 48. Body member 20 may also have a passage 62 extending from the lateral end 24 of body member 20 in a direction generally parallel to its longitudinal axis 26 for receiving a locking member 68. The passage 62 may open into the passage 28 so that the locking member 68 contacts locking member 48 to further secure the components of the implant 10 in position. In alternative embodiments, there may be two passages 28, and passage 62 may be eliminated, as shown in FIGS. 5 and 8.

Figure 29:
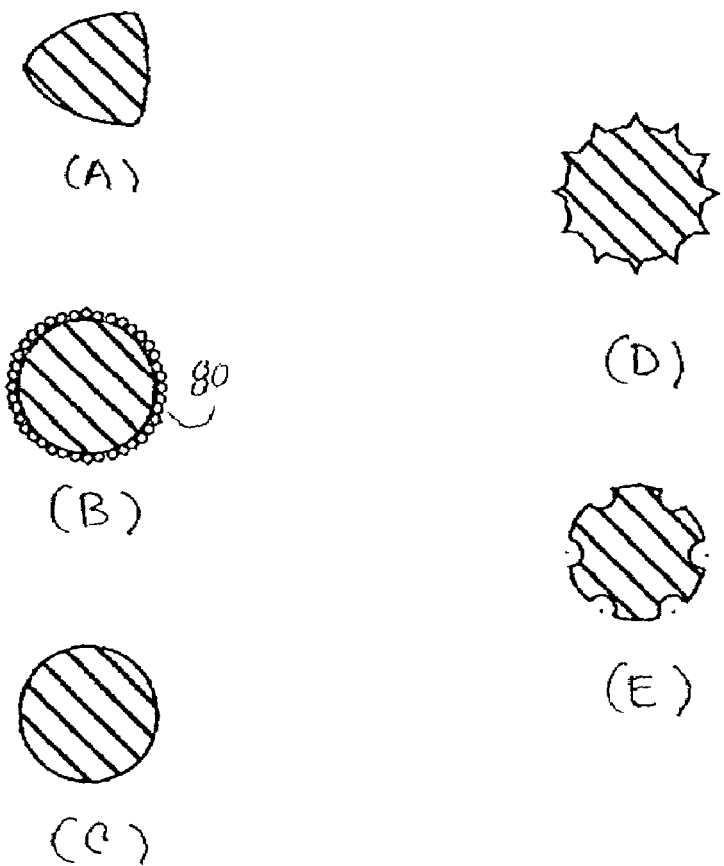
FIG. 29 illustrates exemplary cross-sectional configurations of the body member and/or rod.

The body member 20 may be made in a variety of cross-sectional configurations, examples of which are shown in FIG. 29. Examples of cross-sectional configurations of the body member 20 include circular (C), circular with beads (B) or another bone in-growth enhancing surface, triangular (A) to complement the cross-sectional shape of the natural femoral neck 8, scalloped (E), and fluted (D). Those skilled in the art will appreciate that a number of cross-sectional configurations may be employed. The triangular, scalloped, and fluted cross-sectional configurations constrain or restrict the body member 20 against rotational movement about its axis following implantation. As bone in-growth progresses around the body member 20, the implant 10 will be further constrained against rotation.

The body member 20 is configured to accommodate the anatomical constraints of the recipient of the implant. Typical dimensions range from about 50 mm to 120 mm in length and from about 12 mm to 30 mm in diameter. For adult female patients, the natural femoral neck 8 varies in diameter from about 14 mm to 22 mm. For adult male patients, the natural femoral neck 8 varies from about 16 mm to 34 mm in diameter. The length and diameter of the body member 20 will necessarily be less than the diameter of the proximal femur 6 and the natural femoral neck 8 in which the implant 10 is positioned.

Rod 40 has a longitudinal axis 146, a distal end 44 and a proximal end 42. In one embodiment of rod 40, there is a second engagement surface 50 positioned at proximal end 42. The second engagement surface 50 may form a protrusion, as shown in FIGS. 2, 4, 6, 7, 9, 13, 15, 19 and 20, or may form a recess as shown in FIGS. 10, 11, 12, 14, 16, 17 and 21. The second engagement surface 50 is configured to complement the first engagement surface 30 of the body member 20.

Figure 2A:
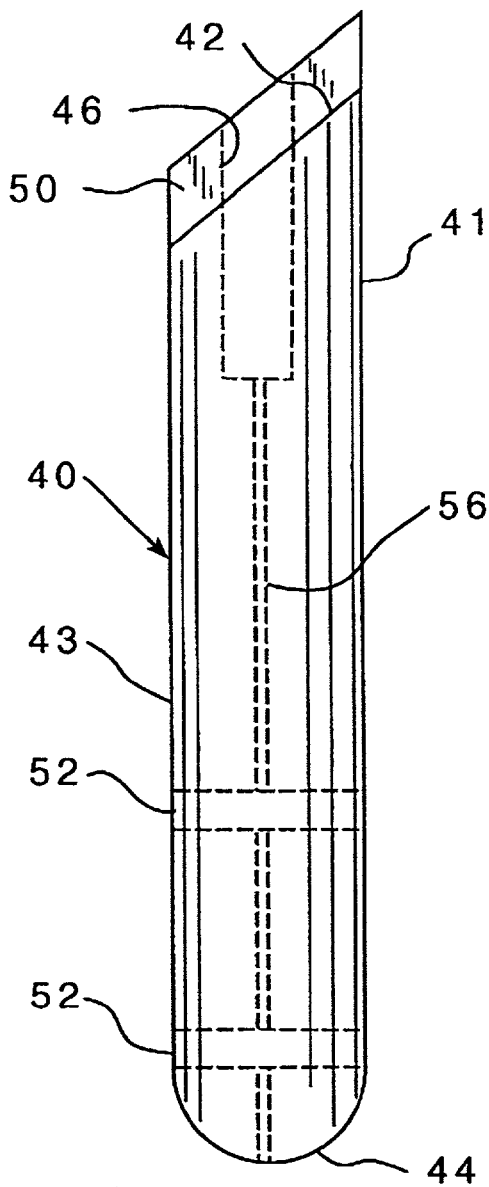
FIG. 2A is a side view of an embodiment of a rod showing an engagement surface that is trapezoidal in cross-section.
Figure 2B:
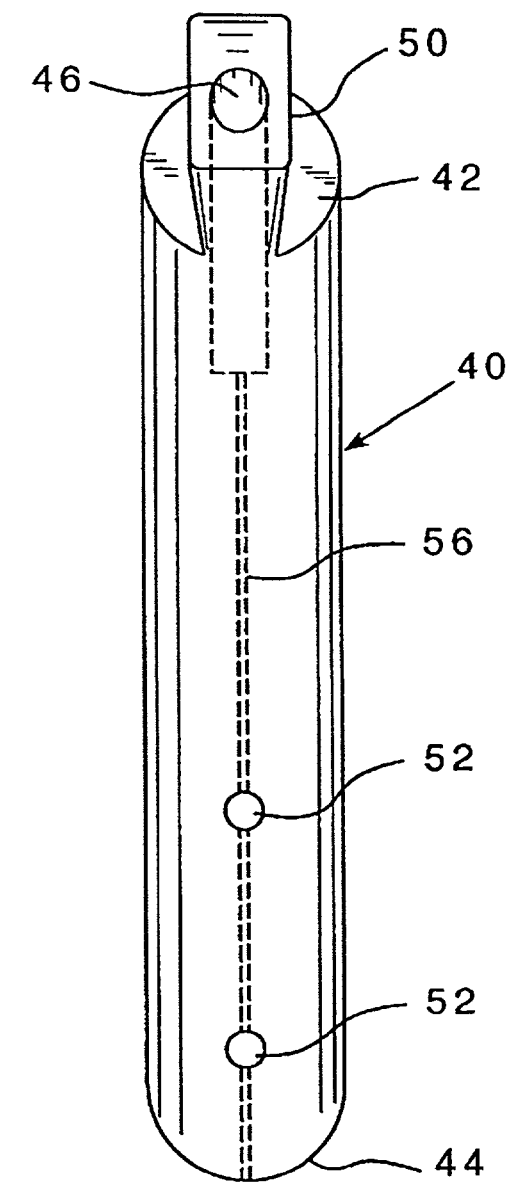
FIG. 2B is a front view of the rod of FIG. 2A.
Figure 4A:
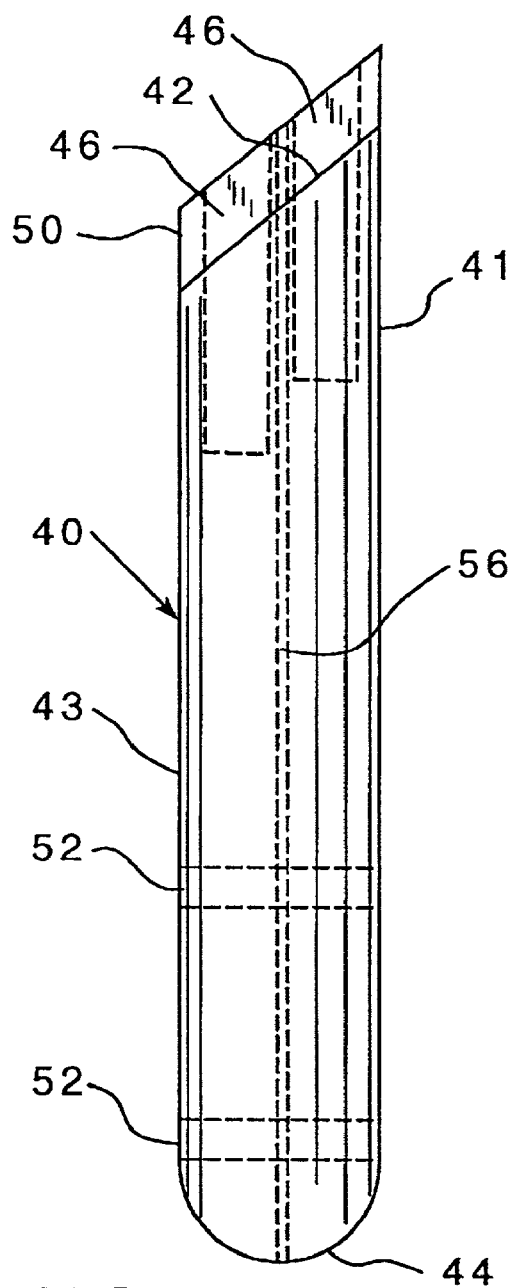
FIG. 4A is a side view of an alternative embodiment of a rod.
Figure 4B:
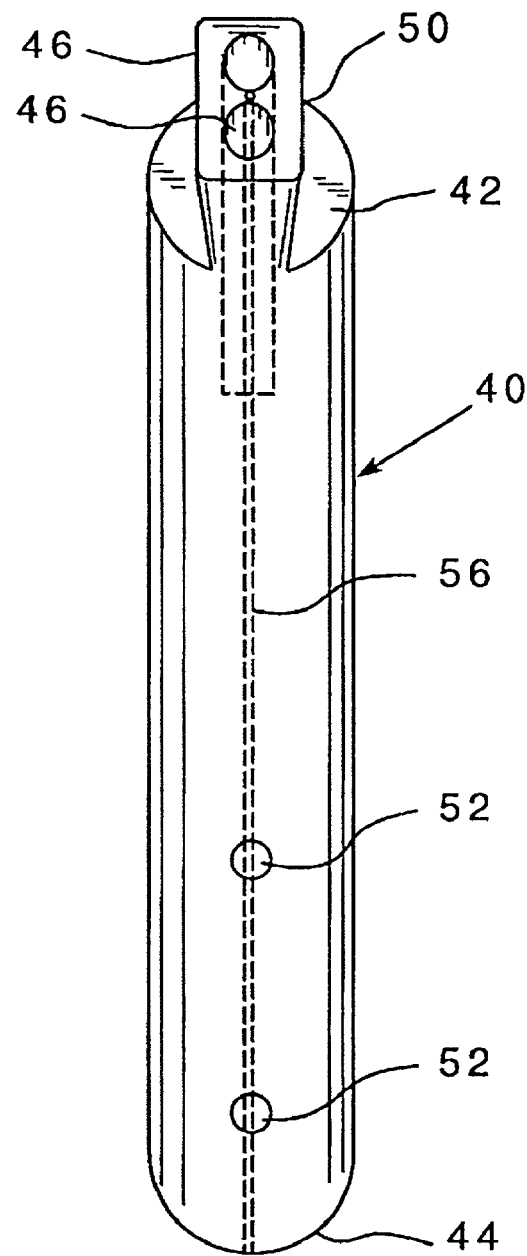
FIG. 4B is a front view of the rod of FIG. 4A.
Figure 6A:
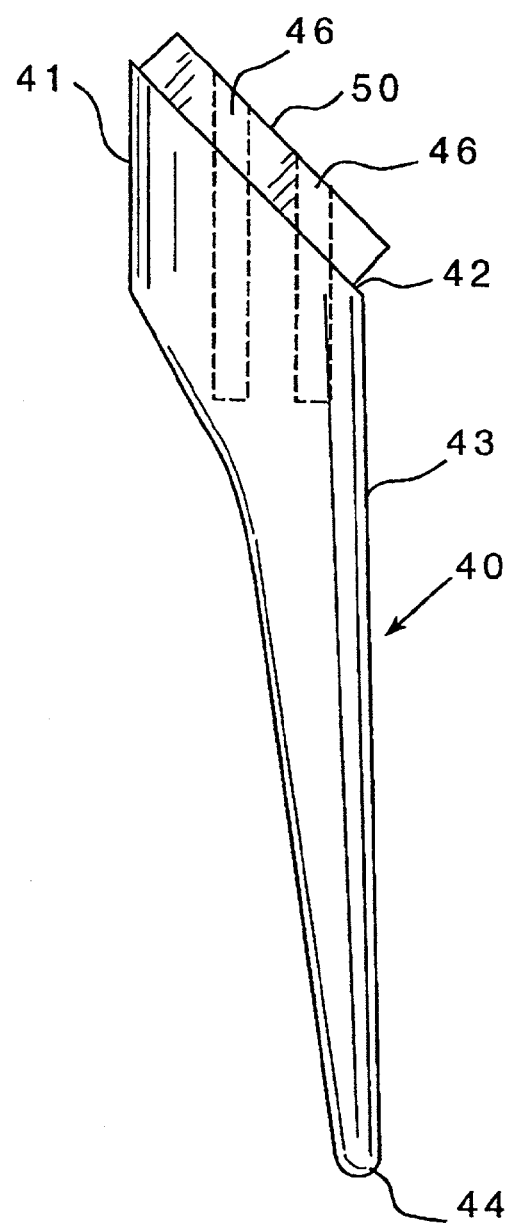
FIG. 6A is a side view of an alternative embodiment of a rod.
Figure 6B:
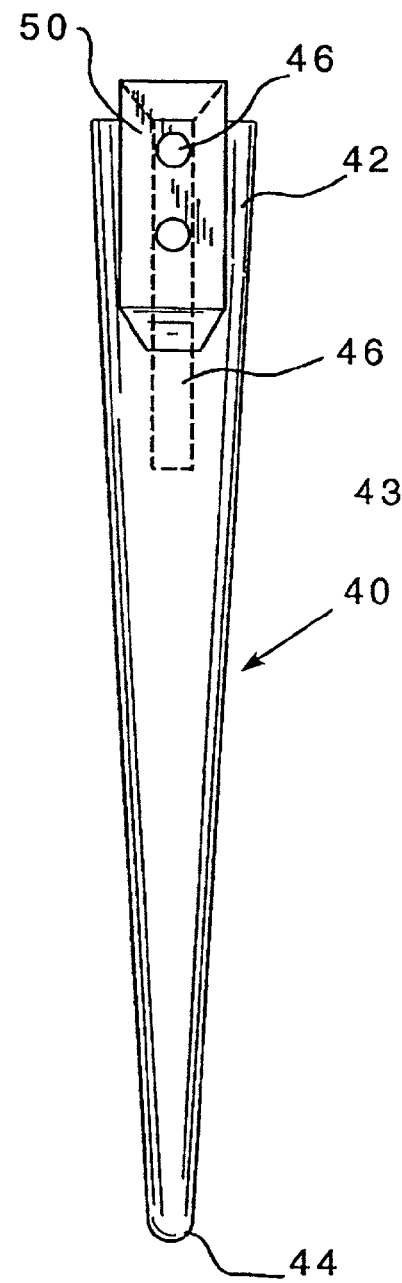
FIG. 6B is a front view of the rod shown in FIG. 6A.
Figure 7:
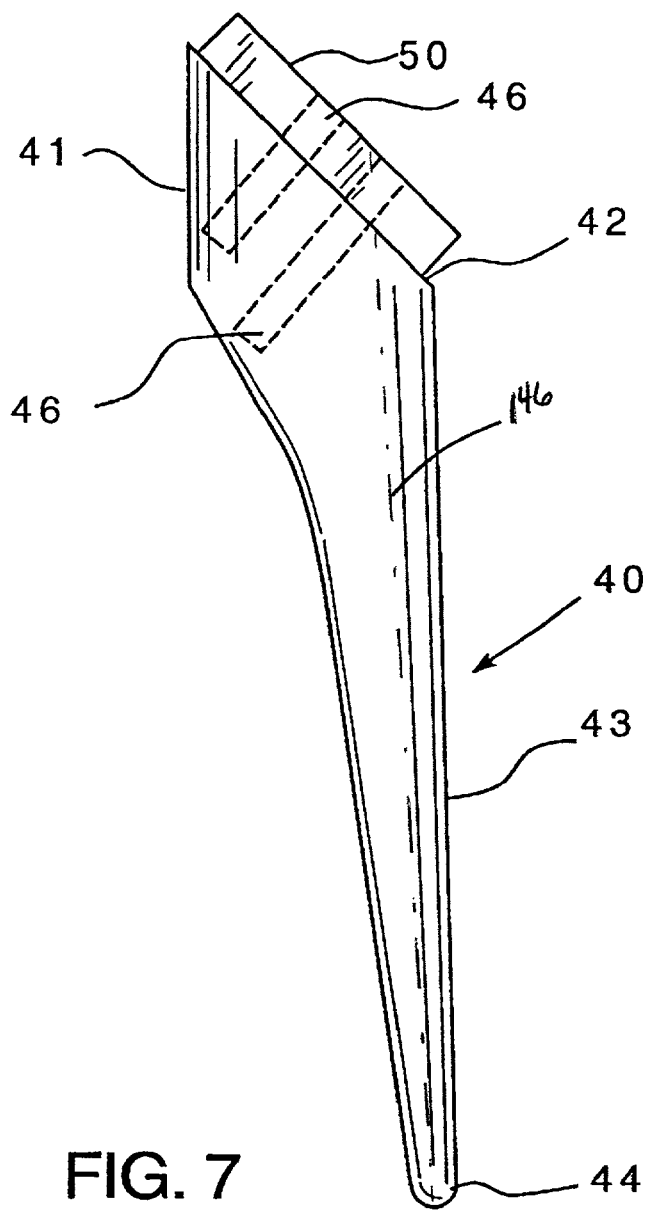
FIG. 7 is a side view of another embodiment of a rod showing locking passages entering at an angle relative to the longitudinal axis of the rod.
Figure 9:
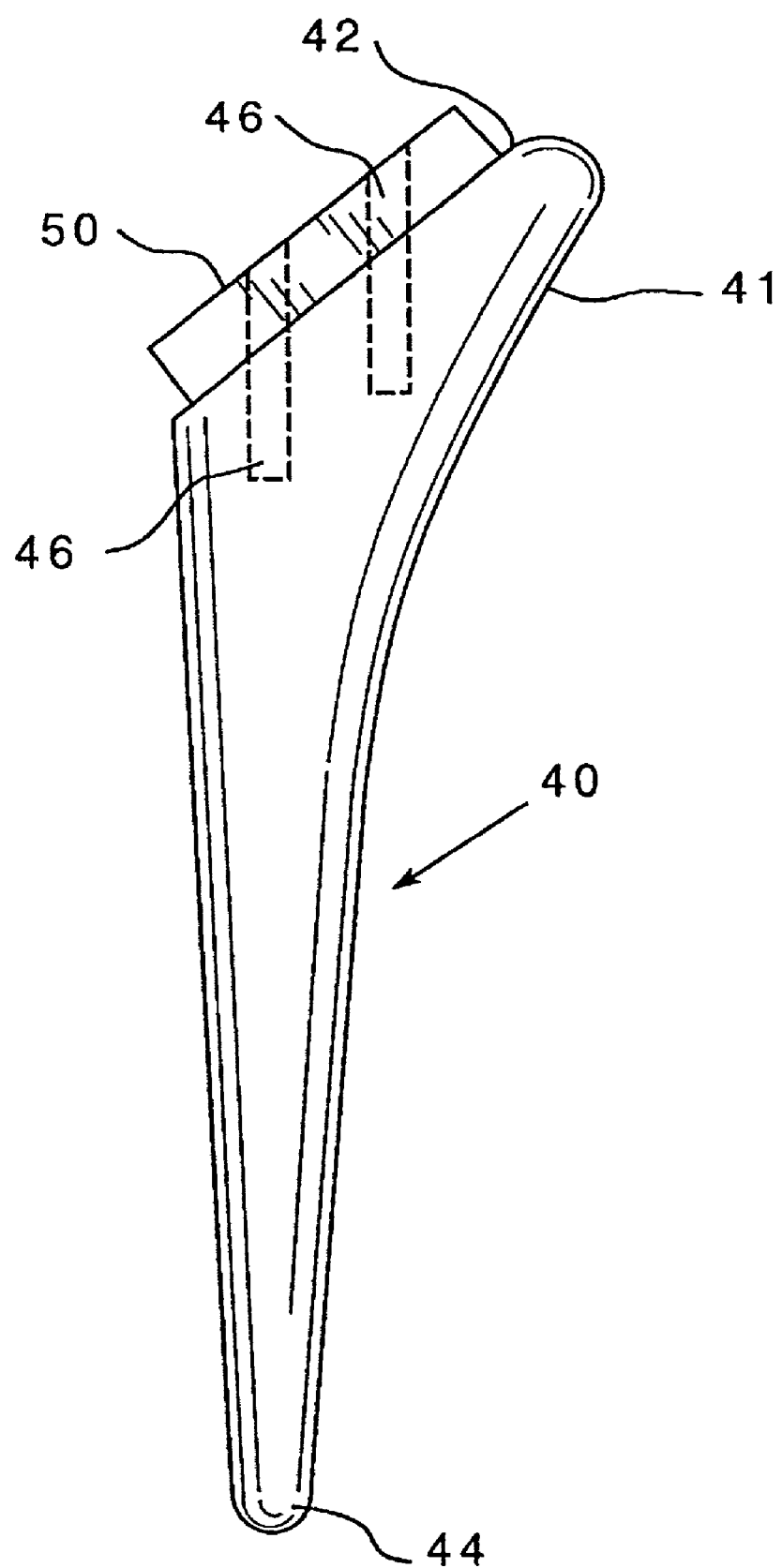
FIG. 9 is a side view of another embodiment of a rod.

The rod 40 may be made in a variety of configurations. For example, the cross-sectional configuration of the rod 40 may be substantially constant from the proximal end 42 to the distal end 44, as shown in FIGS. 2A, B and 4. However, the cross-sectional configuration of the rod 40 need not be constant and may taper from the proximal end 42 to the distal end 44, as shown in FIGS. 6, 7 and 9. For example, one embodiment of the rod 40 has a cross-sectional configuration of a tapered wedge. Another embodiment forms a dual tapered, or elongated diamond shaped wedge, in cross-section. The dual tapered wedge preferably tapers gradually from the proximal end 42 to the distal end 44 of the rod 40 and ends in a flat, rounded or pointed tip. An alternative embodiment of the rod 40 has a greater cross-sectional dimension at the proximal end 42 of the rod 40 and a lesser cross-sectional dimension at the distal end 44. In one such embodiment shown in FIGS. 6 and 7, the greater dimensioned area at the proximal end 42 has straight medial 41 and lateral 43 sides. In the embodiment shown in FIG. 9, the lateral side 43 is relatively straight and the medial side 41 tapers in a gradual curve from the greater dimensioned proximal end 42 to the smaller dimensioned distal end 44. The cross-sectional configuration of the rod 40 may have many shapes, including, but not limited to those shown in FIG. 29; circular (C), circular with a beaded coating to promote bone in-growth (B), rectangular (not shown), dual tapered (not shown), triangular (A), scalloped (E) or fluted (D). Those skilled in the art will appreciate that a number of configurations may be employed. An advantage of some of the varying configurations is that they are able to restrict rotational movement of the rod 40 after implantation until bone in-growth progresses enough to secure the implant 10 in position.

The embodiment of rod 40 shown in FIGS. 2A, B may typically be from about 12 to 21 cm in length, and preferably about 12 to 16 cm, and most preferably about 14.6 cm in length. This embodiment of rod 40 may be from 10 to 25 mm in diameter, and preferably between 12-15 mm, and more preferably about 13.5 mm in diameter. Those skilled in the art will recognize that rod 40 can be made in various lengths and diameters to accommodate most, if not all, male and female patients.

The variations in sizes of the implant 10 will fall within the anatomical ranges and constraints of the patient population. In order to accommodate patient differences, the various modular components of the implant 10 of the present invention can be made in a variety of sizes that are interchangeable with other components. The implant 10 may also be sized for implantation in children.

As stated previously, the body member 20 has a first engagement surface 30 and the rod 40 has a second engagement surface 50. The first and second engagement surfaces, 30 and 50 respectively, are configured for complementary engagement with each other.

The first engagement surface 30 is located on the side of the body member 20 that will face distally when implanted. The second engagement surface 50 of the embodiment of rod 40 that is exemplified by FIGS. 2A, B, is located on the proximal end 42 of the rod 40. In an embodiment of the implant 10 of the present invention, the first engagement surface 30 comprises a recess for receiving the second engagement surface 50, and the second engagement surface 50 comprises a protrusion configured for complementary engagement with the recess. In another embodiment of the implant 10 of the present invention, the second engagement surface 50 comprises a recess for receiving the first engagement surface 30, and the first engagement surface 30 comprises a protrusion configured for complementary engagement with the recess. As shown in FIGS. 11 through 17, the recess and the protrusion can have a variety of configurations, including, but not limited to, cylindrical, square shaped, dovetailed, T-shaped, rectangular, pyramidal, trapezoidal, domed and irregularly shaped. In addition, both the recess and the protrusion can have a range of sizes, as defined by their lengths and widths, which will be limited by the size of the body member 20 and the size of the rod 40.

The above types of engagement between the first and second engagement surfaces 30 and 50, respectively, increase the stability of the modular components of the implant 10 by constraining the body member 20 against rotation about its axis 26 and by preventing rotation and separation of the body member 20 and rod 40 relative to each other. It is believed that the implant of the present invention transfers mechanical stress to the bone, which is well suited to bear the stress. While a screw or fastener is not required in the embodiments described, a locking member 48, such as a setscrew, or a locking member having a Morse taper, or other fastening means may be provided.

Referring to FIGS. 10A, B, an embodiment of the first and second engagement surfaces 30 and 50, respectively, is shown wherein the first engagement surface 30 is on an exterior side of the cylindrical body member 20 and the second engagement surface 50 is in the form of a concave trough sized to receive and seat a portion of the cylindrical body member 20. In this embodiment, a locking member 48 is provided to lock the body member 20 and the rod 40 in position relative to each. At least one locking passage 28 in a direction transverse to the longitudinal axis 26 of the body member 20 is provided in the body member 20 and at least one locking passage 46 is provided in the rod 40 to receive the locking member or members 48. The passage or passages 46 are positioned for axial alignment with the passage or passages 28 of the body member 20 when the two components are implanted. The passages 28, 46 may be threaded to receive a screw or may be smooth and have a slightly smaller diameter or dimension than that of the locking member 48 to allow the locking member 48 to be wedged into the passages 28, 46 to create a pressure fit between the locking member 48 and the passages. The locking member 48 may be further secured by locking member 68. Locking member 68 may be a threaded setscrew, or other suitable means for securing locking member 48 in position.

Figure 1B:
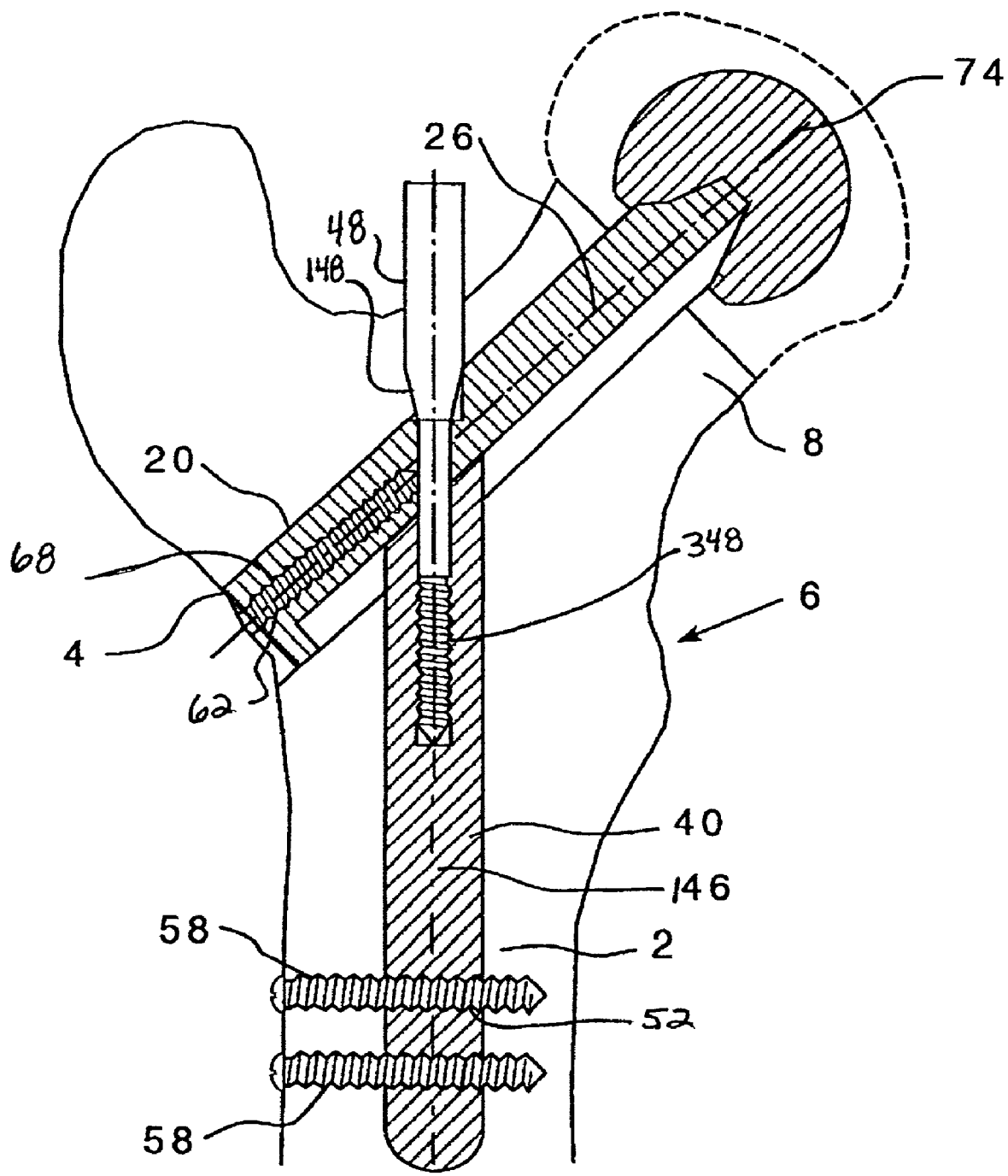
FIG. 1B is a cross-sectional view of an assembled embodiment of the implant of the present invention having an alternative embodiment of a locking member and alternative positioning of stabilizing members, shown as implanted in a femur.
Figure 19:
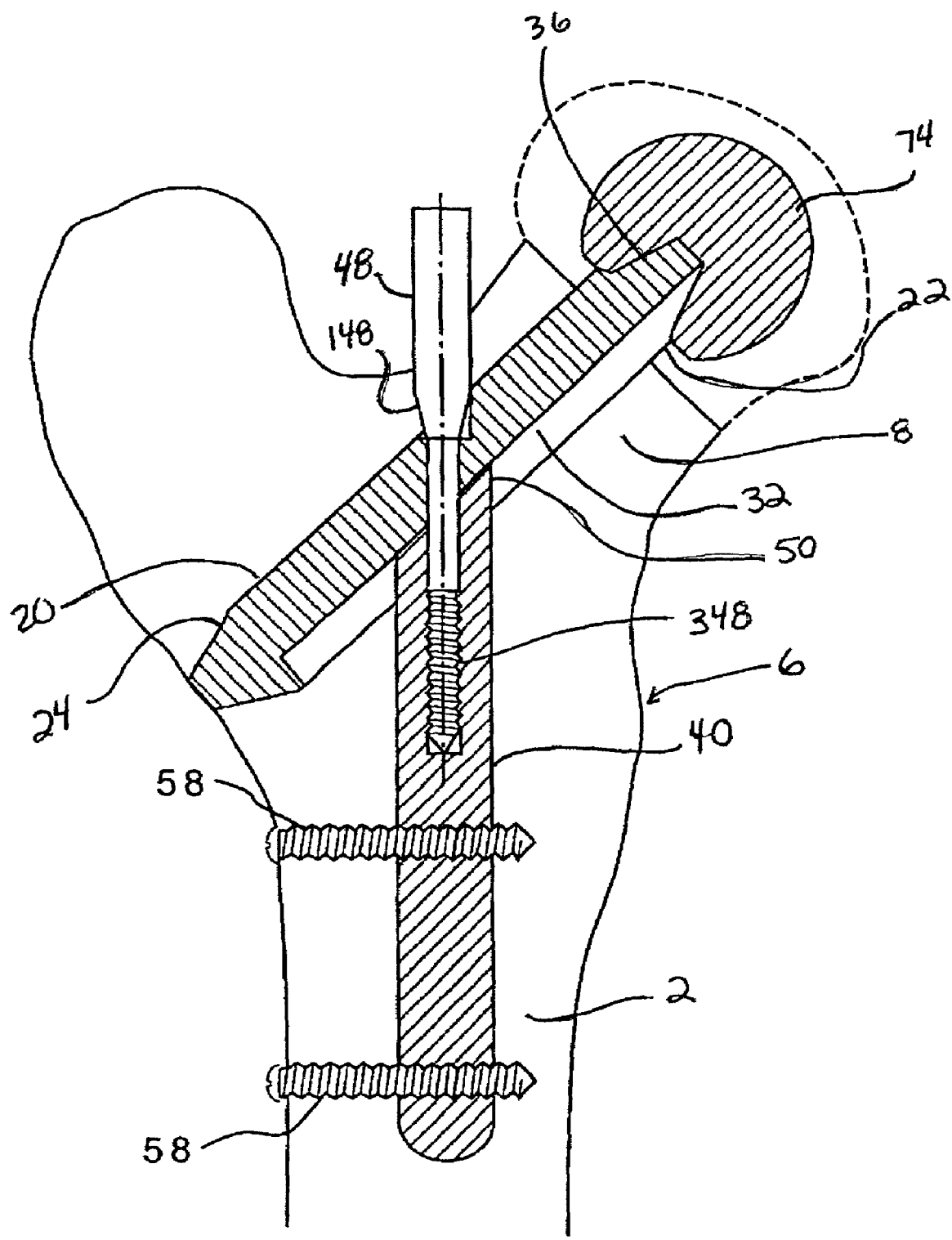
FIG. 19 is a cross-sectional view of an alternative embodiment of a rod and body member without a locking screw through the medial end of the body member.
Figure 20:
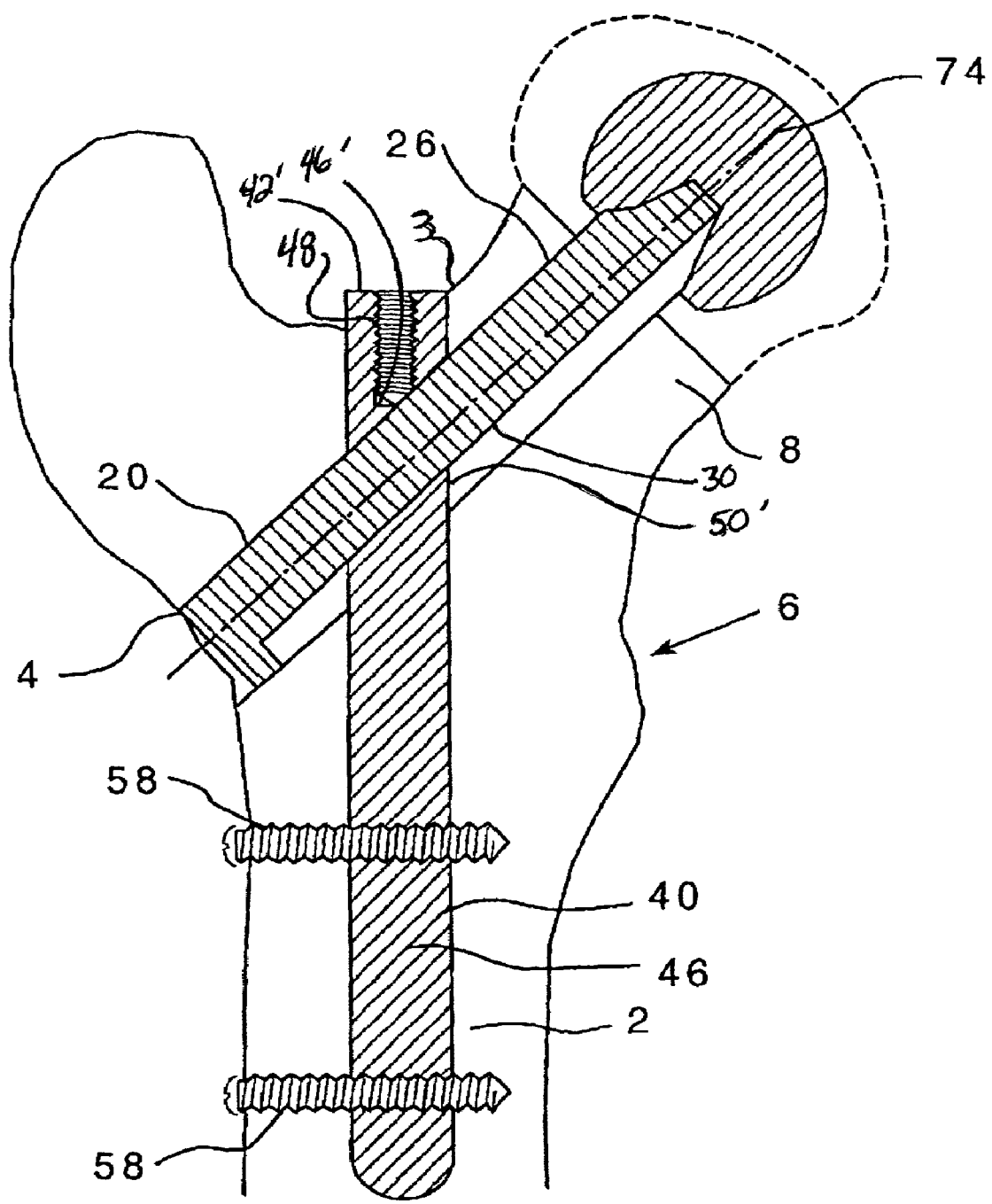
FIG. 20 illustrates a cross-sectional view of an alternative embodiment of the invention showing an elongate rod and body member therethrough wherein the second engagement surface of the rod is formed as a protrusion for engagement with the recessed first engagement surface of the body member.
Figure 21:
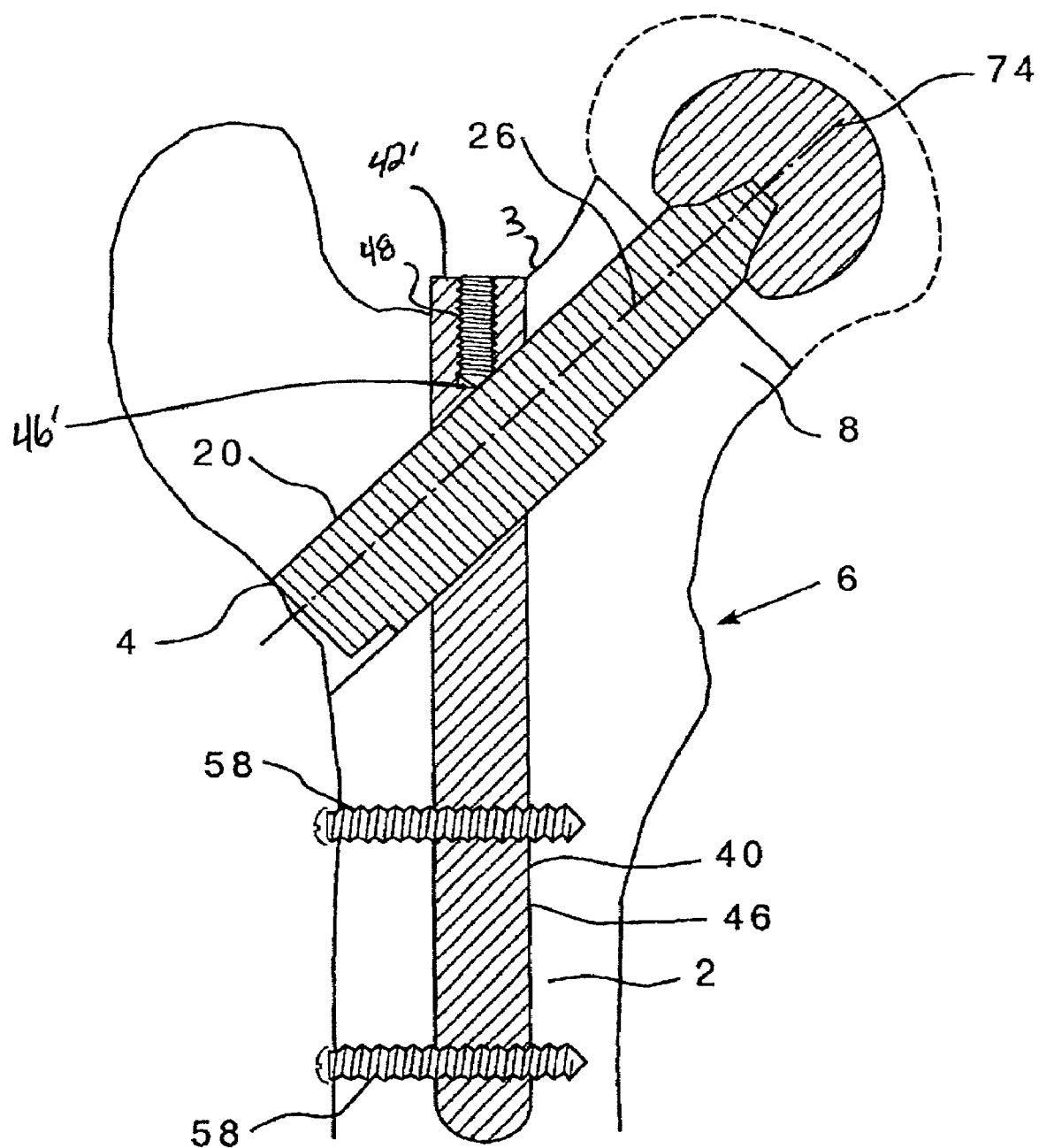
FIG. 21 illustrates the embodiment of the rod of FIG. 20 wherein the second engagement surface is recessed and the first engagement surface forms a protrusion.
Figure 22:
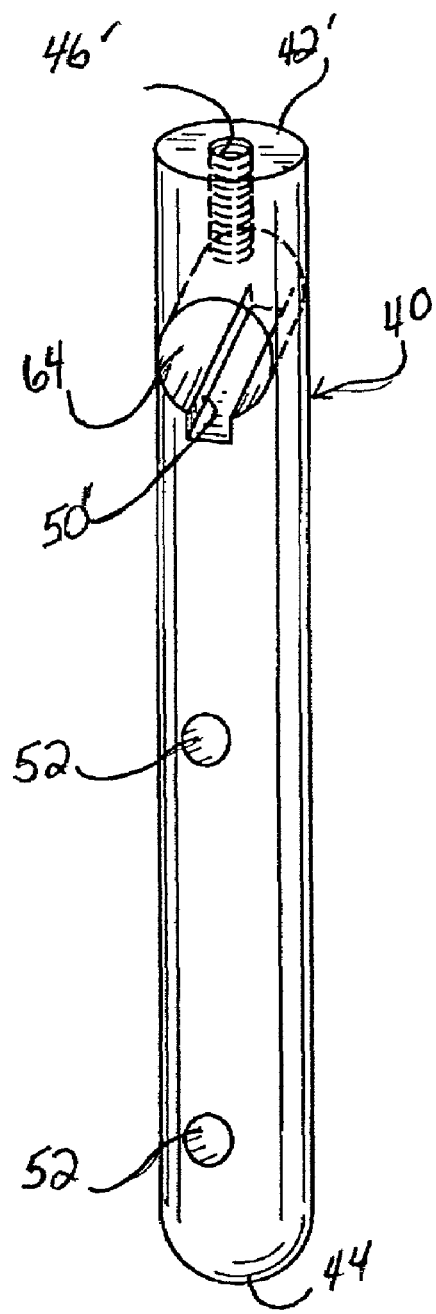
FIG. 22 illustrates a view of the rod of FIG. 21.
Figure 23:
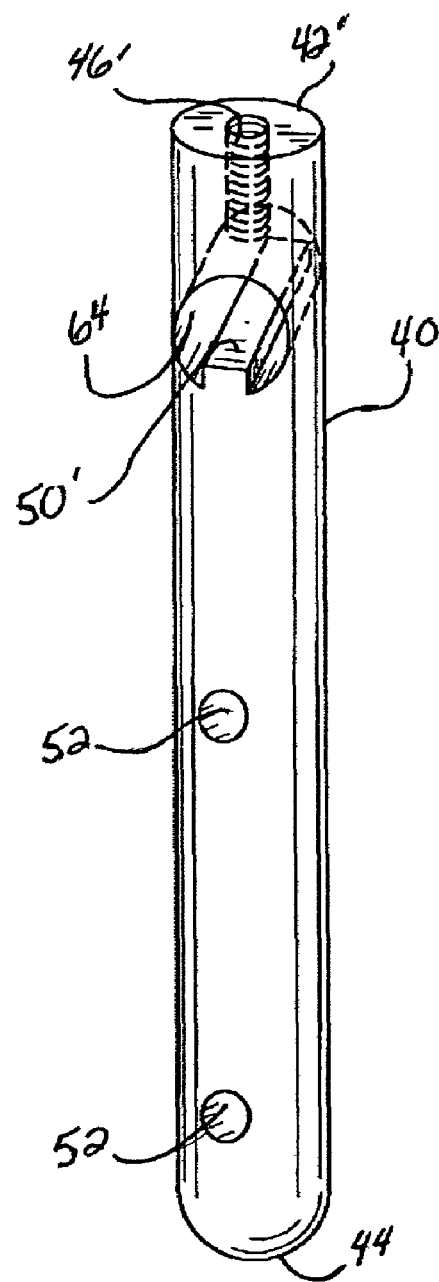
FIG. 23 illustrates a view of the rod of FIG. 20.

As shown in FIGS. 1A, 1B and 19, the locking member 48 may be configured for a pressure fit through the body member 20 and threaded into at least a portion of the rod 40. The locking member 48 shown in FIG. 1A has a first taper 148 for wedging engagement through the body member 20 and a second taper 248 for wedging engagement through the proximal end of the rod 20 and a threaded end portion 348 for threaded engagement with the lower portion of passage 46 of rod 40. In the embodiment shown in FIG. 1B, the locking member 48 has the first taper 148 and is uniformly cylindrical to the threaded end portion 348. The passages 28, 46 as shown for example, in FIGS. 1A, B and 10-17, are formed to pass through the first and second engagement surfaces 30, 50.

The passage 46 may be substantially coaxial with the longitudinal axis 146 of the rod 40, or generally parallel to it. Alternatively, the passage 46 may be positioned at an angle transverse to the longitudinal axis 146 of the rod 40, as shown in FIG. 7.

The implant 10 may also include a passage 52 that passes through at least a portion of the rod 40 in a direction transverse to the longitudinal axis 126 of the rod 40 for stabilizing the implant 10 in the femur 6, as shown for example, in FIGS. 1, 2, 4 and 10A-17A. The passage 52 may be located towards the distal end 44 of the rod 40, or anywhere along the length of the rod 40 suitable for stabilizing the rod 40 in the femur. In addition, the rod 40 may have more than one passage 52. The implant may further comprise a fastener or other stabilizing member or members 58 for insertion through the passage 52. Preferably, the stabilizing member 58 is a bone screw, but may be anything that would stabilize the rod 40 within the intramedullary canal 2 of the femur 6.

The rod 40 may also have a guide passage 56. The guide passage 56 extends the full length of the rod 40 and may be co-axial to the longitudinal axis 146 of the rod 40. The guide passage 56 assists a surgeon in guiding the rod 40 into the proper position within the femur 6. In use, after the intramedullary canal 2 is reamed by a succession of increasingly larger sized reamers to gradually increase the size of the opening, the surgeon inserts a guide wire into the intramedullary canal 2. When the wire is positioned as desired, the surgeon inserts the guide passage 56 of rod 40 over the guide wire to lead the rod 40 to the desired position within the canal 2. The surgeon then pulls the guide wire through the guide passage and out of the intramedullary canal 2.

Figure 24:
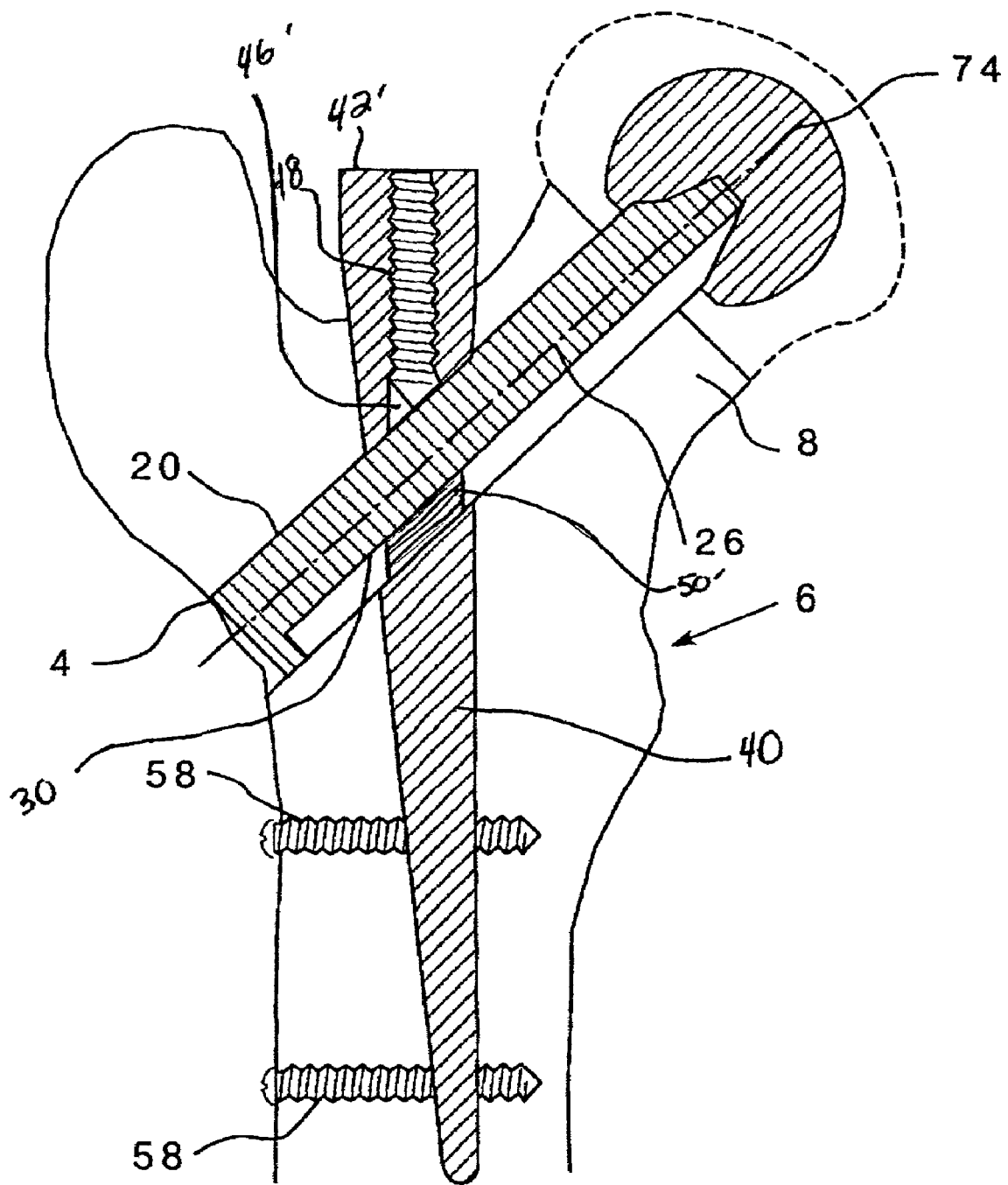
FIG. 24 illustrates an alternative embodiment of the elongate rod implanted in a patient'femur.
Figure 25:
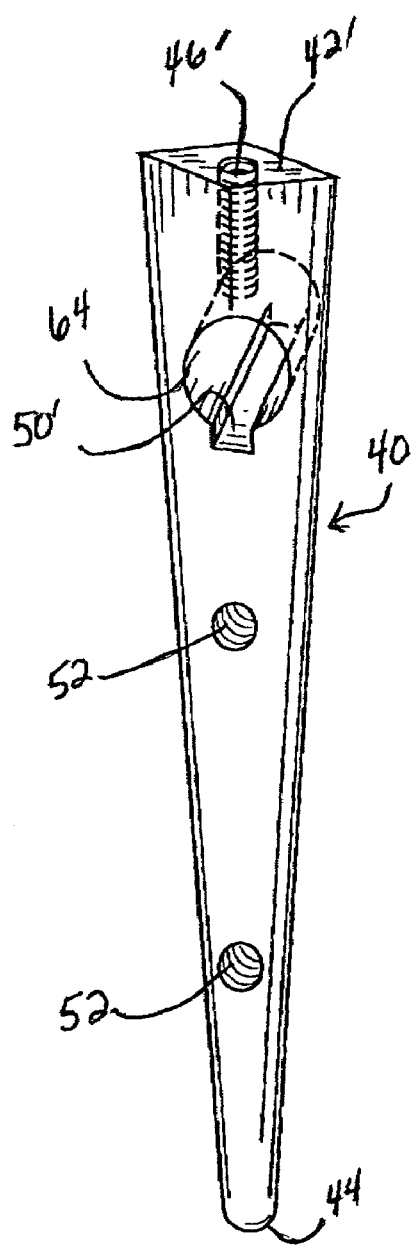
FIGS. 25 and 26 illustrate alternative embodiments of the rod of FIG. 24 configured to receive a setscrew designed for a pressure fit against the body member.
Figure 26:
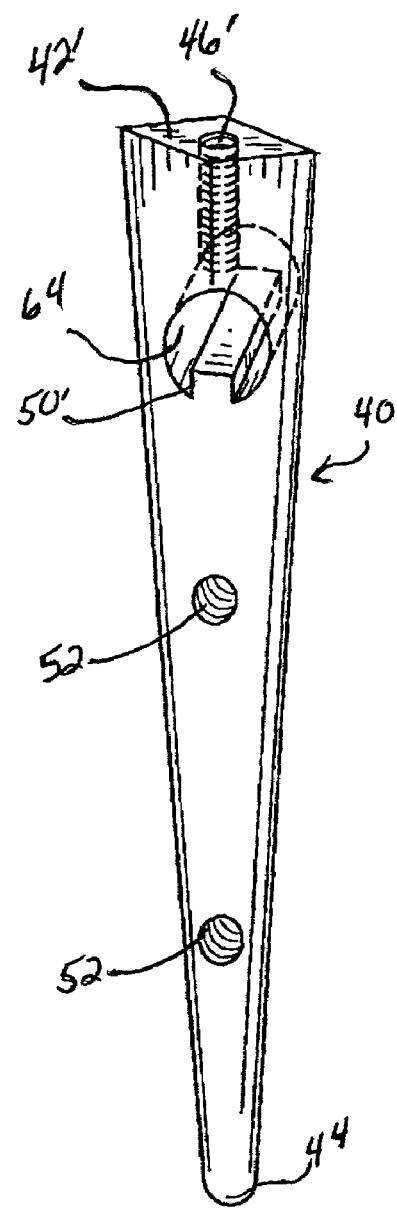
Figure 27:
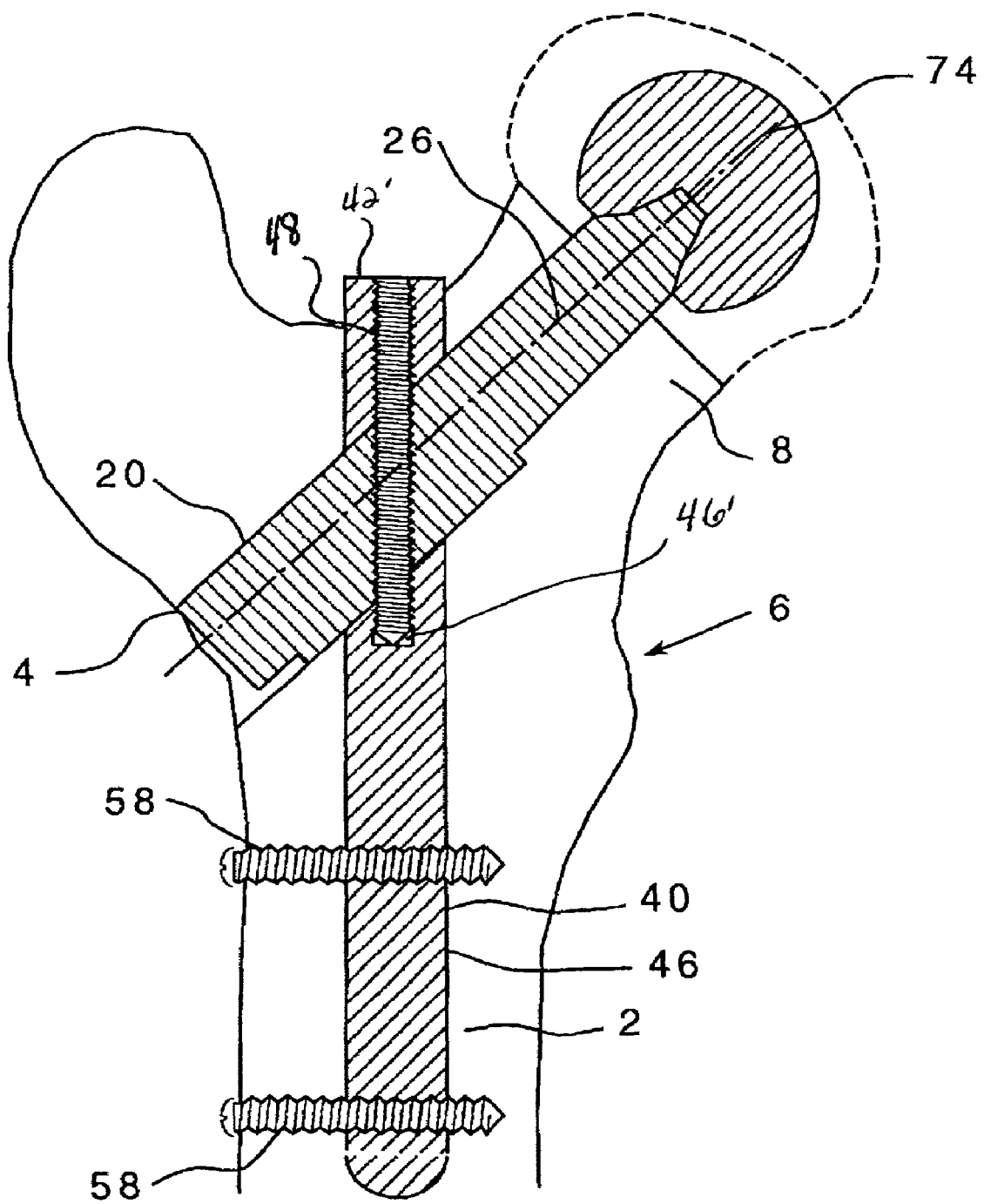
FIG. 27 illustrates an alternative embodiment of the elongate rod and body member implanted in a patient's femur showing a locking screw passing through the body member.
Figure 28:
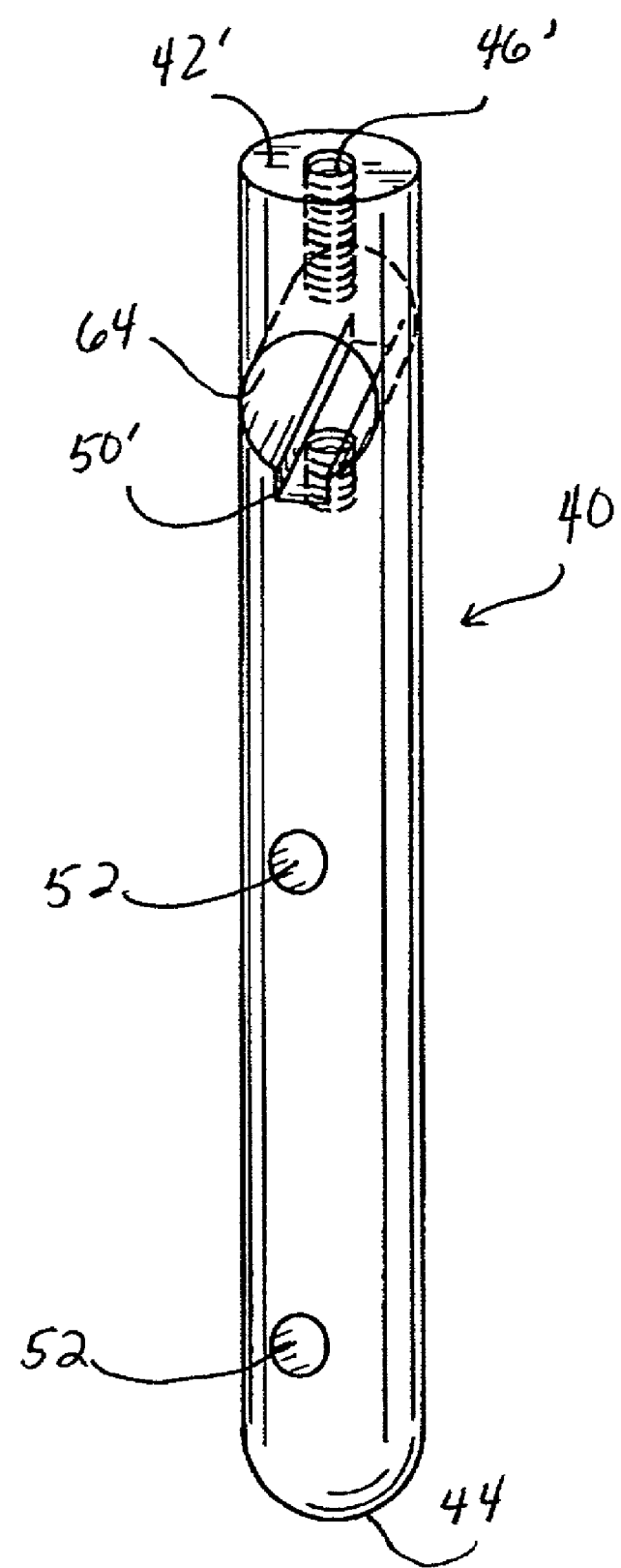
FIG. 28 illustrates the rod of FIG. 27.

In an alternative embodiment of rod 40 shown in FIGS. 20 to 28, rod 40 is longer than the embodiment described above, extending from the proximal most end 3 of the femur 6 into the intramedullary canal 2. Rod 40 includes a proximal end 42', a distal end 44 and a transverse passage 64. The transverse passage 64 in this embodiment is angled relative to the longitudinal axis of the rod to position the body member 20, in use, through the femoral neck and towards the femoral head. A second engagement surface 50', similar to the engagement surface 50, is provided within the passage 64. The engagement surface 50' can be formed as a recess or a protrusion, in a variety of configurations similar to those shown in FIGS. 10A to 17A as discussed herein. A passage 46' is provided for receipt of a locking member 48. Passage 46' may extend to and open into the passage 64 so that the locking member 48 can be pressure fit against body member 20, as shown in FIGS. 20-26, or may extend through and beyond passage 64 as shown in FIGS. 27 and 28. Although passage 46' is shown as threaded, it may also be smooth to accommodate a locking member 48 as shown in FIG. 1A or 1B. The rod 40 in this embodiment may be cylindrical in shape, as shown in FIGS. 20-23, 27 and 28, or may be tapered or wedge shaped, as shown in FIGS. 24-26. Those skilled in the art will recognize that other cross-sectional configurations, such as those shown in FIG. 29, may be employed. The proximal end 42' may extend beyond the proximal end 3 of the femur 6 as shown in FIGS. 24 and 27, or may be generally co-terminus with proximal end 3.

In addition to the various embodiments of the implant 10 described above, the implant 10 may include other features and embodiments that were also disclosed in U.S. Pat. Nos. 6,284,002 and 6,616,697, which are both incorporated herein by reference.

Figure 18:
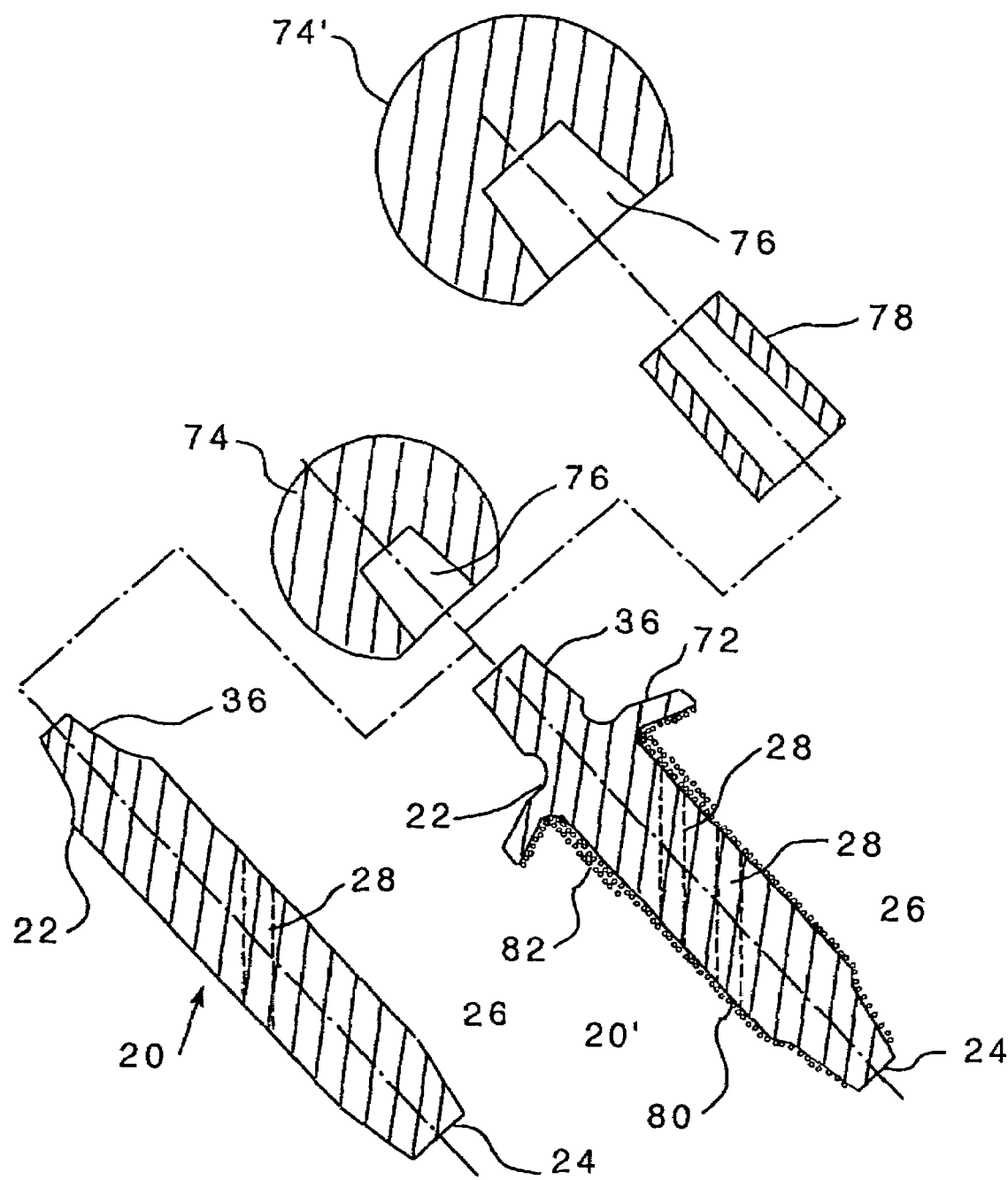
FIG. 18 represents an exploded cross-sectional view of alternative embodiments of a body member, with a head member and an optional sleeve.
Figure 30:
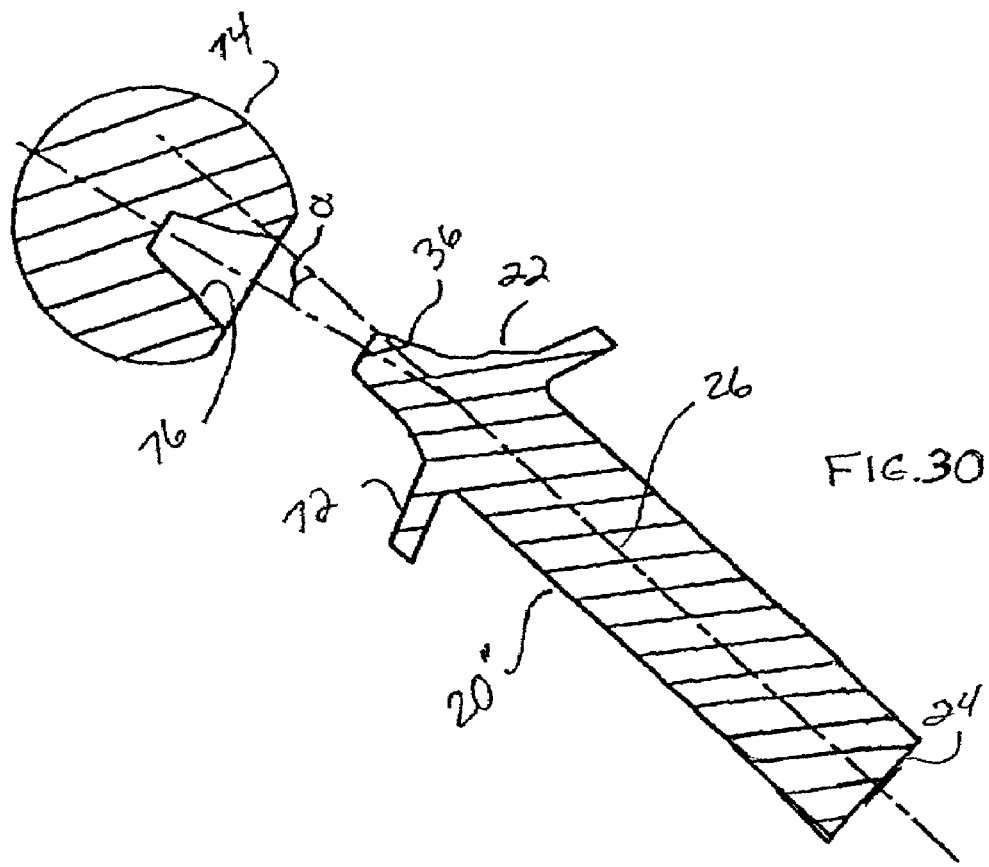
FIG. 30 illustrates a body member having a joining portion disposed at an angle from the longitudinal axis of the body member.

For example, as illustrated in FIGS. 18 and 30, the body member 20 may contain a collar 72. The collar 72 aids in properly distributing the forces applied to the femur 6. In the embodiment having a collar 72, the body member 20 would be inserted through the medial side of the bone following removal of the femoral head. The implant 10 therefore would further include a head member 74. The head member 74 is designed to engage the joining portion 36 of the medial end 22 of the body member 20 and also engage a patient's acetabulum. The head member 74 may contain a recess 76 to join the head member 74 to the joining portion 36 of the body member 20. Alternatively, (not shown), the medial end 22 of the body member 20 may contain a recess as the joining portion and the head member 74 may contain a protrusion to allow the head member 74 to join the medial end 22 of the body member 20. The head member 74 may be co-axial relative to the axis 26 of the body member 20, as shown in FIG. 18, or may be anteverted relative to the axis 26 at an angle α, as shown in FIG. 30.

In addition, the implant 10 may also include a sleeve 78, as shown in FIG. 18. The sleeve 78 is designed to alter either the angle at which the head member 74 extends from the body member 20, if anteversion is desired, or the distance of the head member 74 from the body member 20. Sleeves 78 of various sizes and angles may be provided to accommodate a variety of patient anatomies.

The implant 10 may have a porous coating 80 to promote bone in-growth. In addition, the implant 10 may also have a second layer of coating 82. The porous coatings, 80 and 82, may be found on at least a portion of the surface of the body member 20, the underside of the collar 72, if any, and on at least a portion of the surface of the rod 40. The coatings may also cover the entire surface of the rod 40 and body member 20.

Any biocompatible material may be employed for the materials of the present invention. Suitable materials include, but are not limited to, stainless steel, titanium and cobalt. Any biocompatible textures or coatings that engage the bone or that promote bone in-growth may be utilized with the present invention.

The implant 10 may be inserted in a patient using any of a number of suitable surgical techniques. One method for insertion comprises forming a first incision on the lateral side of the patient's hip over the flare 4 of the greater trochanter. A second incision is formed over the patient's proximal hip, near the waist, in a position known by surgeons as being suitable for the starting point of a femoral nail. The femoral head is resected through the first and second incisions, and the intramedullary canal 2 of the femur 6 is reamed through the second incision. A series of standard reamers of gradually increasing size to gradually expand the area for insertion of the rod may be used at the discretion of the surgeon. A guide wire is inserted into the reamed intramedullary canal 2 of the femur, and the rod 40 slides over the guide-wire into the reamed canal 2. The reamed canal may be narrower than the outer dimension of the rod 40 to allow the rod 40 to be pressure fit into the intramedullary canal 2. When the rod 40 is in a desired position, the guide wire is removed.

The method further includes forming a passage from the flare of the greater trochanter along the longitudinal axis of the natural femoral neck. The body member 20 is inserted through the incision, with the joining portion 36 and end 22 leading. The body member 20 is advanced through the passage, aligning the engagement surface 30 and 50 of the body member and the rod, to a desired position. The method may further include locking the body member 20 in the desired position by engaging the locking member 48 into passages 28 and 46, and securing a prosthetic femoral head 74 to the joining portion 36 of the body member 20. If anteversion is desired or a longer length needed, the sleeve 78 may be inserted over the joining portion 36 before the femoral head 74 is attached. The rod 40 may be stabilized in the canal 2 by insertion of one or more screws 58 through passages 52. The relative positions of the body member 20 and the rod 40 may be further secured by insertion of a screw or other locking member 68 through passage 62. The method proceeds by securing a prosthetic femoral head 74 to the joining portion 36 of the body member 20. If anteversions desired or a greater distance between the body member and the acetabulum is required, the sleeve 78 is slipped over the joining portion 36 of the body member 20. Then, the head member is positioned in the opening of the sleeve 78.

Those of ordinary skill in the art will appreciate that various changes in the details, methods, materials and arrangement of parts which have been herein described and illustrated in order to explain the nature of the invention may be made by the skilled artisan within the principle and scope of the invention as expressed in the appended claims.

What is claimed is:

1. An implant system for replacing the proximal portion of a femur having a substantially intact natural femoral neck, medial side and lateral side, the implant comprising:
   a plurality of modular components of varying sizes within anatomical ranges for accommodating varying patient body dimensions, the components comprising:
   a body member having a medial end, a lateral end and a longitudinal axis extending between the medial and lateral ends, the body member being configured for positioning, in use, in a natural femoral neck, and having a first engagement surface on a surface thereof comprising a recess, a joining portion on the medial end and at least one passage therethrough in a direction transverse to the longitudinal axis of the body member;
   a head member having a domed portion configured for positioning, in use, in a natural or prosthetic acetabulum and a joining end for attachment to the joining portion of the body member;
   a rod having a proximal end, a distal end and a longitudinal axis extending between the distal and proximal ends thereof, the rod being configured for positioning, in use, in the intramedullary canal of a femur, the rod having a second engagement surface comprising a protrusion configured for complementary engagement with the recess of the first engagement surface of the body member for securing the body member against rotation about the longitudinal axis of the body member, the rod having at least one bore extending in the proximal end thereof, each such bore being positioned for coaxial alignment, in use, with a corresponding one of the at least one passage through the body member;
   at least one locking member, each such locking member configured for insertion, in use, through and engagement with one of the at least one passage of the body member and the at least one bore of the rod in alignment therewith; and,
   at least one passage through the rod in a direction transverse to the longitudinal axis of the rod.

2. The implant system recited in claim 1 wherein the protrusion having grooves defined therein; and, the recess is a channel has a rail like surface for sliding engagement with the grooves on the protrusion.

3. The implant system recited in claim 1 wherein the protrusion having rail-like surfaces defined therein; and, the recess is a channel has grooves for sliding engagement with the rail-like surfaces on the protrusion.

4. The implant system recited in claim 1 wherein the protrusion is trapezoidal in cross-section in an anterior to posterior direction.

5. The implant system recited in claim 1 wherein the protrusion is square in cross-section.

6. The implant system recited in claim 1 wherein the protrusion is rectangular in cross-section in an anterior to posterior direction.

7. The implant system recited in claim 1 wherein the protrusion is T-shaped in cross-section in an anterior to posterior direction.

8. The implant system recited in claim 1 wherein the protrusion is dome shaped.

9. The implant system recited in claim 1 wherein the protrusion defines an irregular shape.

10. The implant system recited in claim 1 wherein the protrusion is pyramidal in cross-section.

11. The implant system recited in claim 1 wherein the protrusion and the recess have complementary dovetailed engagement surfaces.

12. The implant system recited in claim 1 wherein the rod gradually tapers from its proximal end to its distal end.

13. The implant system recited in claim 1 wherein the rod is circular in cross-section and uniform along a major portion of its length.

14. The implant system recited in claim 1 wherein the rod has a substantially uniform medial side and a tapered lateral side defining an area of greater dimension at the proximal end of the rod and an area of lesser dimension at the distal end of the rod.

15. The implant system recited in claim 1 further comprising a collar positioned at the medial end of the body member and configured for abutting contact, in use, with a surface of the resected femoral neck.

16. The implant system recited in claim 1 wherein the joining portion extends outwardly from the body member at an acute angle relative to the longitudinal axis of the body member.

17. The implant system recited in claim 16 wherein the head member has a recess for receiving the joining portion of the body member.

18. The implant system recited in claim 1 wherein the joining portion extends outwardly from the body member in substantial coaxial alignment relative to the longitudinal axis of the body member.

19. The implant system recited in claim 18 wherein the head member has a recess for receiving the joining portion of the body member.

20. The implant system recited in claim 1 further comprising a first surface coating on at least a portion of the body member for promoting bone in-growth into the coating following implantation.

21. The implant system recited in claim 20 further comprising a second surface coating on at least a portion of the first surface coating.

22. The implant system recited in claim 1 further comprising a first surface coating on at least a portion of the rod for promoting bone in-growth into the coating following implantation.

23. The implant system recited in claim 22 further comprising a second surface coating on at least a portion of the first surface coating.

24. The implant system recited in claim 1 wherein the body member is configured in cross-section to inhibit rotational motion of the body member following implantation.

25. The implant system recited in claim 24 wherein the body member is fluted in cross-section.

26. The implant system recited in claim 24 wherein the body member is scalloped in cross-section.

27. The implant system recited in claim 1 wherein the body member is circular in cross-section.

28. The implant system of claim 1 wherein the rod is a dual wedge in cross-section, wherein the dual wedge gradually tapers from the proximal end to the distal end.

29. The implant system recited in claim 1 wherein the rod is configured in cross-section to inhibit rotational motion of the rod about the longitudinal axis thereof following implantation.

30. The implant system recited in claim 29 wherein the rod is fluted in cross-section.

31. The implant system recited in claim 29 wherein the rod is scalloped in cross-section.

32. The implant system recited in claim 29 wherein the rod is generally triangular in cross-section.

33. The implant system recited in claim 1 wherein the rod has a guide passage extending from the proximal to the distal ends thereof.

34. The implant system recited in claim 1 further comprising at least one stabilizing member, each such stabilizing member being configured for passage through and engagement with one of the at least one passage of the rod.

35. The implant system recited in claim 1 further comprising a locking passage through at least a portion of the lateral end of the body member in a direction substantially coaxial to the longitudinal axis of the body member.

36. The implant system recited in claim 35 further comprising a locking screw for passage into the locking passage of the body member.

37. The implant system recited in claim 1 including a sleeve member for positioning between the head member and the joining portion of the body member for optionally altering the position of the domed portion of the head member relative to the body member.

38. The implant system recited in claim 37 wherein the sleeve is longer than the joining portion for extending the distance between the head member and the body member.

39. A method for implanting a proximal femoral replacement implant into a patient using at least one reamer having a cutting portion, said method comprising:

forming a first incision on the lateral side of the patient's hip in a position external to the flare of the greater trochanter;

forming a second incision on the lateral side of the patient's proximal thigh near the waist;

resecting the head of the femur;

reaming the intramedullary canal of the femur;

inserting a guide wire into the intramedullary canal of the femur;

sliding a rod over the guide wire into the intramedullary canal of the femur, the rod having a proximal end, a distal end and a longitudinal axis extending between the distal and proximal ends thereof, and having an engagement surface thereon;

removing the guide wire;

forming a passage from the flare of the greater trochanter, through one or both of the first and second incisions along the longitudinal axis of the natural femoral neck;

providing a body member having a medial end, a lateral end and a longitudinal axis extending between the medial and lateral ends, and an engagement surface on a side surface thereof and a joining portion on the medial end thereof;

inserting the medial end of the body member through the first incision, and advancing the body member through the passage;

aligning the engagement surfaces of the rod and the body member;

advancing the body member through the passage to a position in which the medial end of the body member extends beyond the resected surface of the femoral neck;

locking the body member in the desired position; and, securing a prosthetic femoral head to the joining portion of the body member.

40. The method of claim 39 wherein a plurality of reamers is used when forming the passages, each of the plurality of reamers having cutting portions of different diameters and different sizes.

41. The method of claim 39 further comprising forming a stabilizing passage through the femur, the stabilizing passage passing from one side of the femur to the other side of the femur and passing through the distal end of the rod.

42. The method of claim 41 further comprising inserting a stabilizing member through the stabilizing passage in the femur and the rod; and tightening the stabilizing member within the femur.

43. An implant system for replacing the proximal portion of a femur having a substantially intact natural femoral neck, medial side and lateral side, the implant comprising:

a plurality of modular components of varying sizes within anatomical ranges for accommodating varying patient body dimensions, the components comprising:

a body member having a medial end, a lateral end and a longitudinal axis extending between the medial and lateral ends, the body member being configured for positioning, in use, in a natural femoral neck, and having a first engagement surface on a surface thereof comprising a protrusion, a joining portion on the medial end and at least one passage therethrough in a direction transverse to the longitudinal axis of the body member;

a head member having a domed portion configured for positioning, in use, in a natural or prosthetic acetabulum and a joining end for attachment to the joining portion of the body member;

a rod having a proximal end, a distal end and a longitudinal axis extending between the distal and proximal ends thereof, the rod being configured for positioning, in use, in the intramedullary canal of a femur, the rod having a second engagement surface comprising a recess in the proximal end the rod, said recess defining a channel through said rod configured to receive the protrusion for securing the body member against rotation about the longitudinal axis of the body member, the rod having at least one bore extending in the proximal end thereof, each such bore being positioned for coaxial alignment, in use, with a corresponding one of the at least one passage through the body member;

at least one locking member, each such locking member configured for insertion, in use, through and engagement with one of the at least one passage of the body member and the at least one bore of the rod in alignment therewith; and, at least one passage through the rod in a direction transverse to the longitudinal axis of the rod.

44. The implant system recited in claim 43 wherein the rod has a guide passage extending from the proximal to the distal ends thereof.

45. The implant system recited in claim 43 further comprising a locking passage through at least a portion of the lateral end of the body member in a direction substantially coaxial to the longitudinal axis of the body member.

46. The implant system recited in claim 45 further comprising a locking screw for passage into the locking passage of the body member.

47. The implant system recited in claim 43 further comprising at least one stabilizing member, each such stabilizing member being configured for passage through and engagement with one of the at least one passage of the rod.

48. The implant system recited in claim 43 wherein the protrusion has grooves defined therein; and, the channel has a rail like surface for sliding engagement with the grooves on the protrusion.

49. The implant system recited in claim 43 wherein the protrusion has dovetailed surfaces defined therein; and, the channel has dovetailed surfaces for sliding engagement with the dovetailed surfaces on the protrusion.

50. The implant system recited in claim 43 wherein the protrusion has rail-like surfaces defined therein; and, the channel has grooves for sliding engagement with the rail-like surfaces on the protrusion.

51. The implant system recited in claim 43 wherein the protrusion is trapezoidal in cross-section in an anterior to posterior direction.

52. The implant system recited in claim 43 wherein the protrusion is square in cross-section.

53. The implant system recited in claim 43 wherein the protrusion is rectangular in cross-section in an anterior to posterior direction.

54. The implant system recited in claim 43 wherein the protrusion is T-shaped in cross-section in an anterior to posterior direction.

55. The implant system recited in claim 43 wherein the protrusion is dome shaped.

56. The implant system recited in claim 43 wherein the protrusion defines an irregular shape.

57. The implant system recited in claim 43 wherein the protrusion is pyramidal in cross-section.

58. The implant system recited in claim 43 wherein the rod gradually tapers from its proximal end to its distal end.

59. The implant system recited in claim 43 wherein the rod is circular in cross-section and uniform along a major portion of its length.

60. The implant system recited in claim 43 wherein the rod has a substantially uniform medial side and a tapered lateral side defining an area of greater dimension at the proximal end of the rod and an area of lesser dimension at the distal end of the rod.

61. The implant system of claim 43 wherein the rod is a dual wedge in cross-section, wherein the dual wedge gradually tapers from the proximal end to the distal end.

62. The implant system recited in claim 43 wherein the rod is configured in cross-section to inhibit rotational motion of the rod about the longitudinal axis thereof following implantation.

63. The implant system recited in claim 62 wherein the rod is fluted in cross-section.

64. The implant system recited in claim 62 wherein the rod is scalloped in cross-section.

65. The implant system recited in claim 43 wherein the body member is configured in cross-section to inhibit rotational motion of the body member following implantation.

66. The implant system recited in claim 65 wherein the body member is fluted in cross-section.

67. The implant system recited in claim 65 wherein the body member is scalloped in cross-section.

68. The implant system recited in claim 43 wherein the body member is circular in cross-section.

69. The implant system recited in claim 43 wherein the lateral end of the body member is closed.

70. The implant system recited in claim 43 wherein the joining portion extends outwardly from the body member at an acute angle relative to the longitudinal axis of the body member.

71. The implant system recited in claim 43 including a sleeve member for positioning between the head member and the joining portion of the body member for optionally altering the position of the domed portion of the head member relative to the body member.

* * * * *

UNITED STATES PATENT AND TRADEMARK OFFICE
CERTIFICATE OF CORRECTION

PATENT NO. : 7,247,171 B2  
APPLICATION NO. : 10/095181  
DATED : July 24, 2007  
INVENTOR(S) : Nicholas G. Sotereanos Page 1 of 1

It is certified that error appears in the above-identified patent and that said Letters Patent is hereby corrected as shown below:

Col. 10, Line 62, delete "has" and insert --having--.

Col. 10, Line 65, delete "having" and insert --has--.

Col. 10, Line 66, delete "has" and insert --having--.

Signed and Sealed this

Tenth Day of February, 2009

JOHN DOLL  
*Acting Director of the United States Patent and Trademark Office*